US 8,114,585 B2

(12) United States Patent
Huang

(10) Patent No.: US 8,114,585 B2
(45) Date of Patent: Feb. 14, 2012

(54) METHOD FOR DETERMINING HUMAN IMMUNODEFICIENCY VIRUS (HIV) CORECEPTOR UTILIZATION BY EXAMINING GP41 MOLECULAR DETERMINANTS

(75) Inventor: Wei Huang, Foster City, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 113 days.

(21) Appl. No.: 12/304,418

(22) PCT Filed: Jun. 12, 2007

(86) PCT No.: PCT/US2007/013874
§ 371 (c)(1),
(2), (4) Date: Sep. 9, 2009

(87) PCT Pub. No.: WO2007/146336
PCT Pub. Date: Dec. 21, 2007

(65) Prior Publication Data
US 2010/0047765 A1     Feb. 25, 2010

Related U.S. Application Data

(60) Provisional application No. 60/813,636, filed on Jun. 13, 2006.

(51) Int. Cl.
*C12Q 1/70*     (2006.01)
*C12Q 1/68*     (2006.01)
*A61K 39/21*     (2006.01)

(52) U.S. Cl. ............................ 435/5; 435/6.1; 424/208.1

(58) Field of Classification Search ........................ None
See application file for complete search history.

(56) References Cited

U.S. PATENT DOCUMENTS

| 5,837,464 | A | 11/1998 | Capon et al. |
| 6,420,545 | B1 | 7/2002 | Hoxie et al. |
| 7,097,970 | B2 | 8/2006 | Petropoulos et al. |
| 7,247,439 | B1 | 7/2007 | Richman et al. |

FOREIGN PATENT DOCUMENTS

WO    WO 97/27319     7/1997

OTHER PUBLICATIONS

Pollakis, G., et al., 2001, N-linked glycosylation of the HIV type-1 gp120 envelope glycoprotein as a major determinant of CCR5 and CXCR4 coreceptor utilization, J. Biol. Chem. 276(16):13433-13441.*
Sundaravaradan, V., et al., 2007, Role of HIV-1 subtype C envelope V3 to V5 regions in viral entry, coreceptor utilization and replication efficiency in primary T-lyphocytes and monocyte-derived macrophages, Virol. J., 4(126):1-12.*
Huang, W., et al., 2008, Coreceptor tropism can be influenced by amino acid substitutions in the gp41 transmembrane subunit of human immunodeficiency virus type 1 envelope protein, J. Virol. 82(11):5584-5593.*
Huang, W., et al., 2011, Mutational pathways and genetic barriers to CXCR4-mediated entry by human immunodeficiency virus type 1, Virol. 409:308-318.*
PCT International Search Report dated Jul. 1, 2008, for International Application No. PCT/US2007/013874, filed Jun. 12, 2007.
Allaway et al., 1993, "Synergistic Inhibition of HIV-1 Envelope-Mediated Cell Fusion by CD4-Based Molecules in Combination with Antibodies to Gp120 or Gp41," Aids Res. Hum. Retroviruses, vol. 9:581-587.
Altschul et al., 1990, "Basic Local Alignment Search Tool," J. Mol. Biol., vol. 215:403-410.
Altschul et al., 1997, "Gapped BLAST and PSI-BLAST: A New Generation of Protein Database Search Programs," Nucleic Acids Res., vol. 25:3389-3402.
Baba et al., 1999, "A Small Molecule, Nonpeptide CCR5 Antagonist with Highly Potent and Selective Anti-HIV-1 Activity," Proc. Natl. Acad. Sci., USA, vol. 96:5698-5703.
Baxter et al., 1999, "A Pilot Study of the Short-Term Effects of Antiretroviral Management Based on Plasma Genotypic Antiretroviral Resistance Testing (GART) in Subjects Failing Antiretroviral Therapy," Presented at the $6^{th}$ Conference on Retroviruses and Opportunistic Infections, Chicago, Il.
Bernard, et al., 1993, "The F Plasmid CcdB Protein Induces Efficient ATP-Dependent DNA Cleavage by Gyrase," J. Mol. Biol., vol. 23:534-541.
Bernard, et al., 1992, "Cell Killing by the F Plasmid Ccdb Protein Involves Poisoning of DNA Topoisomerase II Complexes," J. Mol. Biol., vol. 226:735-745.
Bleul, et al., 1996, "The Lymphocyte Chemoattractant Sdf-1 is a Ligand for Lestr/Fusin and Blocks HIV-1 Entry," Nature, vol. 382:829-833.
Bridger et al., 1999, "Synthesis and Structure-Activity Relationships of Phenylenebis(Methylene)-Linked Bis-Azamacrocycles that Inhibit HIV-1 and HIV-2 Replication by Antagonism of the Chemokine Receptor CXCR4," J. Med. Chem., vol. 42:3971-3981.
Brumme et al., 2004, "Clinical and Immunological Impace of HIV Envelop V3 Sequence Variation After Starting Initial Triple Antiretroviral Therapy," AIDS, vol. 18:F1-F9.
Glenn et al., 2004, "A single Amino Acid Change in gp41 is Linked to the Macrophage-Only Replication of Phenotype of a Molecular Clone of Simian Immunodeficiency Virus Derived from the Brain of a Macaque with Neuropathogenic Infection," Virology, vol. 325:297-307.
Hertogs et al., 1998, "A Rapid Method for Simultaneous Detection of Phenotypic Resistance to Inhibitors of Protease and Reverse Transcriptase in Recombinant Human Immunodeficiency Virus Type 1 Isolates from Subjects Treated with Antiretrivoral Drugs," Antimicrob. Agents Chemother., vol. 42:269-276.

(Continued)

*Primary Examiner* — Jeffrey S. Parkin
(74) *Attorney, Agent, or Firm* — Kilpatrick Townsend & Stockton LLP

(57) ABSTRACT

The invention provides a method for determining whether a human immunodeficiency virus is likely to be have enhanced ability to enter a cell expressing CD4 and CXCR4 relative to a reference HIV. In certain aspects, the methods comprise detecting one or more amino acid in an envelope protein of the HIV associated with enhanced ability to enter CD4- and CXCR4-expressing cells and determining that the HIVs ability to enter such cells is enhanced relative to a reference HIV, e.g., an HIV that does not comprise such amino acid(s).

6 Claims, 25 Drawing Sheets

OTHER PUBLICATIONS

Figure 1A:
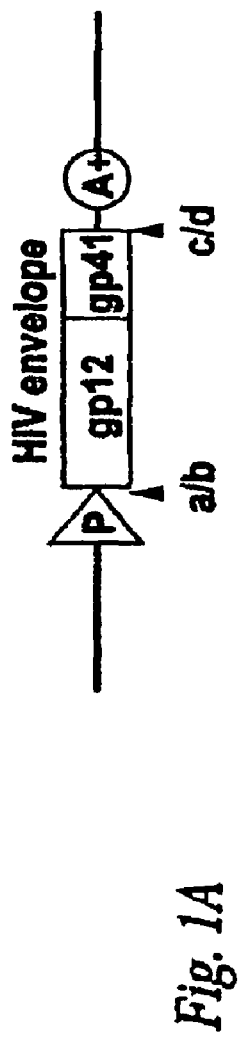

Huang et al., 2008, "Coreceptor Tropism Can Be Influenced by Amino Acid Substitutions in the gp41 Transmembrane Subunit of Human Immunodeficiency Virus Type 1 Envelop Protein," Journal of Virology, vol. 81(11):5584-5593.

Jensen et al., 2003, "Improved Coreceptor Usage Prediction and Genotypic Monitoring of R5-to-X4 Transition by Motif Analysis of Human Immunodeficiency Virus Type 1 env V3 Loop Sequences," J. Virology, vol. 77:13376-13388.

Kilby et al., 1998, "Potent Suppression of HIV-1 Replication in Humans by T-20, a Peptide Inhibitor of Gp41-Mediated Virus Entry," Nat. Med., vol. 4:1302-1307.

Kumar et al., 2004, MEGA3: Integrated Software for Molecular Evolutionary Genetics Analysis and Sequence Alignment, Brief Bioinform, vol. 5(2):150-163.

Petropoulos et al., 2000, "A Novel Phenotypic Drug Susceptibility Assay for HIV-1," Antimicrob. Agents & Chem., vol. 44:920-928.

Phrma, 1999, "New Medicines in Development for AIDS," Pharmaceutical Research and Manufacturers of America.

Reimann et al., 1995, "In Vivo Administration of CD4-Specific Monoclonal Antibody: Effect on Provirus Load in Rhesus Monkeys Chronically Infected with the Simian Immunodeficiency Virus of Macaques," Aids Res. Hum. Retroviruses, vol. 11:517-525.

Richman, D., 1998, "Nailing Down Another HIV Target," Nature Med., vol. 4:1232-1233.

Rimsky et al., 1998, "Determinants of Human Immunodeficiency Virus type 1 Resistance to Gp41-Derived Inhibitory Peptides," J. Virol., vol. 72:986-993.

Sarkar et al., 1990, "The 'Megaprimer' Method of Site-Directed Mutagenesis," Biotechniques, vol. 8(4):404-407.

Schinazi et al., 1999, "Mutations in Retroviral Genes Associated with Drug Resistance," Intl. Antiviral News, vol. 7:46-49.

Stephenson, J., 1999, "New Class of Anti-HIV Drugs," Jama, vol. 282:1994.

Taylor et al., 2008, "An Alteration of Human Immunodeficiency Virus gp41 Leads to Reduced CCR5 Dependence and CD4 Independence," Journal of Virology, vol. 82(11):5460-5471.

Adachi et al., 1986, "Production of Acquired Immunodeficiency Syndrome-Associated Retrovirus in Human and Nonhuman Cells Transfected with an Infectious Molecular Clone," J. Virol., 59:284-291.

Alkhatib et al., 1996, "CC CKR5: A Rantes, MIP-1α, MIP-1β Receptor as a Fusion Cofactor for Macrophage-tropic HIV-1," Science, 272:1955-8.

Carpenter et al., 2000, "Antiretrovial Therapy in Adults," JAMA, 283:381-390.

CDC (Centers for Disease Control and Prevention), 1999, "HIV/AIDS Surveillance Report," 11(No. 1).

Coffin et al., 1995, "HIV Population Dynamics In Vivo: Implications for Genetic Variation, Pathogenesis, and Therapy," Science, 267:483-489.

DHHS (Department of Health and Human Services) et al., Jan. 28, 2000, "Henry Kaiser Family Foundation: Guidelines for the Use of Antiretrovirals Agents in HIV-Infected Adults and Adolescents."

Gerdes et al., 1990, "The hok Killer Gene Family in Gram-Negative Bacteria," The New Biologist, 2(11):946-956.

Hwang et al., 1997, "A Conditional Self-Inactivating Retrovirus Vector that Uses a Tetracycline-Responsive Expression System," J. Virol., 71:7128-7131.

Japour et al., 1993, "Standardized Peripheral Blood Mononuclear Cell Culture Assay for Determination of Drug Susceptibilities of Clinical Human Immunodeficiency Virus Type 1 Isolates," Antimicrob. Agents Chemother., 37:1095-1101.

Judice et al., 1997, "Inhibition HIV Type 1 Infectivity by Constrained α-helical Peptides: Implications for the Viral Fusion Mechanism," Proc. Natl. Acad. Sci., USA, 94:13426-30.

Mascola et al., 2000, "Protection of Macaques Against Vaginal Transmission of a Pathogenic HIV-1/SIV Chimeric Virus by Passive Infusion of Neutralizing Antibodies," Nature Med., 6:207-210.

Miyoshi et al., 1998, "Development of a Self-Inactivating Lentivirus Vector," J. Virol., 72:8150-8157.

Naviaux et al., 1996, "The pCL Vector System: Rapid Production of Helper-Free, High-Titer, Recombinant Retroviruses," J. Virol., 70:5701-5705.

Piketty et al., 1999, "Efficacy of a Five-Drug Combination Including Ritonavir, Saquinavir and Efavirenz in Subjects Who Failed on a Conventional Triple-Drug Regimen: Phenotypic Resistance to Protease Inhibitors Predicts Outcome of Therapy," AIDS, 13:f71-f77.

Porter et al., 1998, "Cationic Liposomes Enhance the Rate of Transduction by a Recombinant Retroviral Vector in Vitro and in Vivo," J. Virol., 72:4832-4840.

Rodriguez-Rosado et al., 1999 "Introduction of HIV Drug-Resistance Testing in Clinical Practice," AIDS, 13:1007-1014.

Schurmann et al., 2004, "SCH D: Antiviral Activity of a CCR5 Receptor Antagonist," Eleventh Conference on Retroviruses and Opportunistic Infections, San Francisco Abstract 140LB.

Who, UNAIDS/World Health Organization, "Report: AIDS Epidemic Update: Dec. 1999."

Wild et al., 1992, "A Synthetic Peptide Inhibitor of HIV Replication: Correlation Between Solution Structure and Viral Inhibition," Proc. Natl. Acad. Sci. USA, 89:10537-10541.

Zennou et al., 1998, "Loss of Viral Fitness Associated with Multiple Gag and Gag-Pol Processing Defects in Human Immunodeficiency Virus Type 1 Variants Selected for Resistance to Protease Inhibitors Iin Vivo," J. Virol., 72:3300-3306.

Ziermann et al., 2000, "A Mutation in HIV-1 Protease, N88S, that Causes in Vitro Hypersensitivity to Amprenavir," J. Virol., 74:4414-4419.

* cited by examiner

PhenoSense HIV Entry Assay

Envelope Expression Vector: pHIVenv

HIV-1 Expression Vector: pHIVluc ΔU3

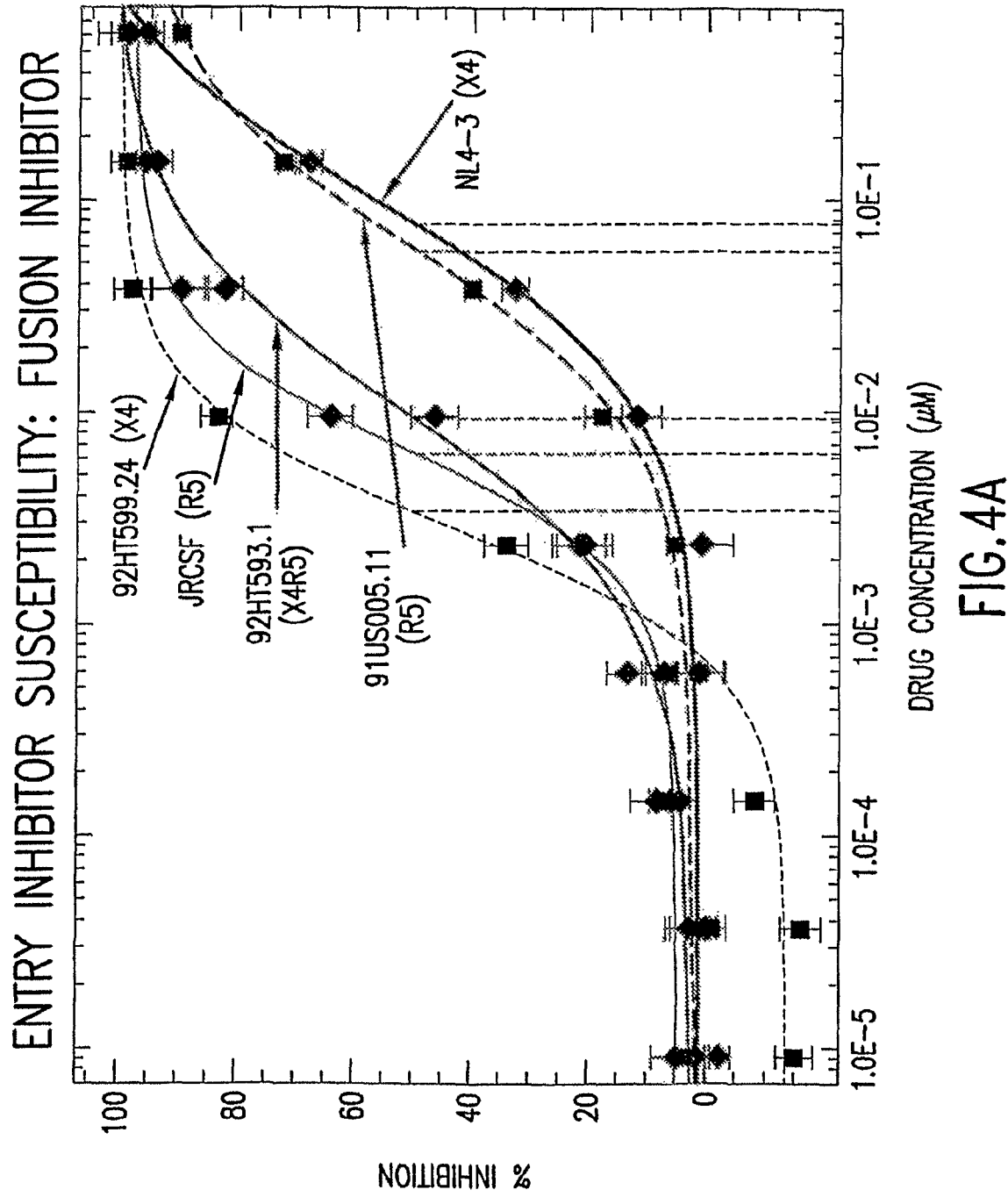

Fig. 12 gp41 envelope sequence

```
                515           529     539
Clone 6    REKRAIGGLGALFLGFLGAAGSTMGAASLTLTAQARQLLSGIVQQQNNLLRAIEAQQHLLQLTVWGIKQLQARVLAVERY
Clone 13   .............................V..................................
Clone 14   .............V....................................................

607                    644 648   654
Clone 6    LQDQQLLGIWGCSGKLICTTDVPWNTSWSNKSLDEIWNNMTWMQWDREINKYTGIIYTLIEDSQIQQEKNEKELLELDKW
Clone 13   .............................A............................................
Clone 14   .............................A......................N..E......D.............

687
Clone 6    ANLWNWFNITNWLWYIKIFIMIVAGLVGLRIVFSVLSIVNRVRQGYSPLSFQTRLPTPRGPDRPEGTEEGGESGRDRSG
Clone 13   .............................................................................
Clone 14   ...........I.................................................................B 767             787 790 792                  812
Clone 6    PLVDGPLAIIWVDLRSLCLFCYHRLRDLLLIVARIVELLGHRGWEILKYWWNLLQYWSQELKKSAISLFNAIAIAVAEGT
Clone 13   .................S..........................R...S...........................
Clone 14   .................S..........................R..R.....................V......

Clone 6    DRIIEIAQRAFRAFLHIPRRIRQGFERALL.
Clone 13   ..............................
Clone 14   ..............................
```

Position according to HXB2

\* Selected clones for chimeras analysis

| clone # | clone ID | Env backbone | V3 loop | Tropism | V3 amino acid sequences |
|---|---|---|---|---|---|
| 1 | 10r (parental) | 10r | 10r | R5 | CTRPGNNTRRSITMGPGRAFYTTGEIIGDIRKAHC |
| 2 | 21d (parental) | 21d | 21d | Dual | ................................... |
| 3 | 86d (parental) | 86d | 86d | Dual | ................................... |
| 4 | 88DV3_10r | 10r | 88d | Dual | ............H..-H.R....KN......... |
| 5 | 88DV3_21d | 21d | 88d | Dual | ............H..-H.R....KN......... |
| 6 | 88DV3_86d | 86d | 88d | Dual | ............H..-H.R....KN......... |
| 7 | 88D (parental) | 88d | c88d | dual | ............H..-H.R....KN......... |
| 8 | 42x V3_10r | 10r | 42x | X4 | ......S...G.LV.-T.R....RN......... |
| 9 | 42x V3_21d | 21d | 42x | Dual | ......S...G.LV.-T.R....RN......... |
| 10 | 42x V3_21d | 86d | 42x | Dual | ......S...G.LV.-T.R....RN......... |
| 11 | 42x (parental) | 42x | 42x | X4 | ......S...G.LV.-T.R....RN......... | substitutions in gp41 of chimeras

| substitution in clone10 | G515 | A539 | D607 | T644 | D648 | E654 | M687 | G746 | C767 | H787 | W790 | I812 |
|---|---|---|---|---|---|---|---|---|---|---|---|---|
| domain in gp41 | FP | FP | HR1-HR2 | HR2 | HR2 | HR2 | TM | CT | CT | CT | CT | CT |
| clone 86gp41 | V | V | A | N | E | D | I | E | S | R | R | V |
| chimera A | V | V | A | N | E | D | I | G | C | H | W | I |
| chimera B | V | V | A | H | D | E | M | G | C | H | W | I |
| chimera C | G | A | D | H | D | E | M | E | S | R | R | V |
| chimera D | G | A | D | N | E | D | I | E | S | R | R | V |

Fig. 19

```
           FP                                                  HR1
          515         529      539
Clone 10  REKRAIGGLGALELGELGAAGSTMGAASLTLTAQARQLLSGIVQQQNNLLRAIEAQQHLLQLTVWGIKQLQARVLAVERY
Clone 21  ...........A...........V........................................................
Clone 86  ...........V....................................................................

HR2   644  648    654
          LQDQQLLGIWGCSGKLICTTDVPWNTSWSNKSLDEIWNNMTWMQWDREINKYTGLIYTLIEDSQIQQEKNEKELLELDKW
              607                                                 N.  E.   D
                                                                              ↓ CT
          TM 687      ANLWNWFNITNWLWYIKIFIMIVAGLVGLRIVFSVLSIVNRVRQGYSPLSFQTRLPTPRGPDRPEGTEEGGESGRDRSG
          ...A............................................................................
          ................I...............................................................
                                                                                    746
                                                    787 790 792                      812
          PLVDGFLALIWVDLRSLCLFCYHRLRDLLLIVARIVELLGHRGWEILKYWWNLLQYWSQELKKSAISLFNAIAIAVAEGT
          ..................................S..............................E............
          ..................................S......R...R.................................

DRLIEIAQRAFRAFLHIPRRIRQGFERALL
          ..............................
          ..............................
```

Clone 10
Clone 21
Clone 86

Clone 10
Clone 21
Clone 86

Clone 10
Clone 21
Clone 86

Clone 10
Clone 21
Clone 86

→ Position used to construct chimeras

Sequences of dual-R clones and R5 clone

SEQUENCE LISTING

```
<160> NUMBER OF SEQ ID NOS: 21

<210> SEQ ID NO 1
<211> LENGTH: 26
<212> TYPE: DNA
<213> ORGANISM: Artificial Sequence
<220> FEATURE:
```

-continued

```
<223> OTHER INFORMATION: synthetic amplification RT primer Primer 1

<400> SEQUENCE: 1
ggagcattta caagcagcaa cacagc                                          26

<210> SEQ ID NO 2
<211> LENGTH: 21
<212> TYPE: DNA
<213> ORGANISM: Artificial Sequence
<220> FEATURE:
<223> OTHER INFORMATION: synthetic amplification RT primer Primer 2

<400> SEQUENCE: 2
ttccagtcav acctcaggta c                                               21

<210> SEQ ID NO 3
<211> LENGTH: 19
<212> TYPE: DNA
<213> ORGANISM: Artificial Sequence
<220> FEATURE:
<223> OTHER INFORMATION: synthetic amplification RT primer Primer 3

<400> SEQUENCE: 3
agaccaatga cttayaagg                                                  19

<210> SEQ ID NO 4
<211> LENGTH: 35
<212> TYPE: DNA
<213> ORGANISM: Artificial Sequence
<220> FEATURE:
<223> OTHER INFORMATION: synthetic amplification 5' PCR primer Primer 4

<400> SEQUENCE: 4
gggctcgaga ccggtcagtg gcaatgagag tgaag                                35

<210> SEQ ID NO 5
<211> LENGTH: 37
<212> TYPE: DNA
<213> ORGANISM: Artificial Sequence
<220> FEATURE:
<223> OTHER INFORMATION: synthetic amplification 5' PCR primer Primer 5

<400> SEQUENCE: 5
gggctcgaga ccggtgagca gaagacagtg gcaatga                              37

<210> SEQ ID NO 6
<211> LENGTH: 36
<212> TYPE: DNA
<213> ORGANISM: Artificial Sequence
<220> FEATURE:
<223> OTHER INFORMATION: synthetic amplification 5' PCR primer Primer 6

<400> SEQUENCE: 6
gggctcgaga ccggtgagca gaagacagtg gcaatg                               36

<210> SEQ ID NO 7
<211> LENGTH: 35
<212> TYPE: DNA
<213> ORGANISM: Artificial Sequence
<220> FEATURE:
<223> OTHER INFORMATION: synthetic amplification 3' PCR primer Primer 7

<400> SEQUENCE: 7
gggtctagaa cgcgttgcca cccatcttat agcaa                                35

<210> SEQ ID NO 8
```

```
<211> LENGTH: 38
<212> TYPE: DNA
<213> ORGANISM: Artificial Sequence
<220> FEATURE:
<223> OTHER INFORMATION: synthetic amplification 3' PCR primer Primer 8

<400> SEQUENCE: 8
gggtctagaa cgcgtccact tgccacccat bttatagc                              38

<210> SEQ ID NO 9
<211> LENGTH: 34
<212> TYPE: DNA
<213> ORGANISM: Artificial Sequence
<220> FEATURE:
<223> OTHER INFORMATION: synthetic amplification 3' PCR primer Primer 9

<400> SEQUENCE: 9
gggtctagaa cgcgtccact tgccacccat btta                                  34

<210> SEQ ID NO 10
<211> LENGTH: 38
<212> TYPE: DNA
<213> ORGANISM: Artificial Sequence
<220> FEATURE:
<223> OTHER INFORMATION: synthetic amplification 3' PCR primer Primer 10

<400> SEQUENCE: 10
gatggtctaa gacgctgttc aatatccctg cctaactc                              38

<210> SEQ ID NO 11
<211> LENGTH: 35
<212> TYPE: PRT
<213> ORGANISM: Artificial Sequence
<220> FEATURE:
<223> OTHER INFORMATION: synthetic HIV-1 envelope protein V3 loop region

<400> SEQUENCE: 11

Cys Thr Arg Pro Gly Asn Asn Thr Arg Arg Ser Ile Thr Met Gly Pro
 1               5                  10                  15

Gly Arg Ala Phe Tyr Thr Thr Gly Glu Ile Ile G

```
Cys Thr Gly Pro Gly Asn Asn Thr Arg Arg Ser Ile His Met Gly His
1               5                   10                  15

Arg Arg Phe Tyr Thr Thr Lys Asn Ile Ile Gly Asp Ile Arg Lys Ala
            20                  25                  30

His Cys

<210> SEQ ID NO 14
<211> LENGTH: 34
<212> TYPE: PRT
<213> ORGANISM: Artificial Sequence
<220> FEATURE:
<223> OTHER INFORMATION: synthetic HIV-1 envelope protein V3 loop region

<400> SEQUENCE: 14

Cys Thr Arg Pro Gly Asn Ser Thr Arg Arg Gly Ile Leu Val Gly Thr
1               5                   10                  15

Arg Arg Phe Tyr Thr Thr Arg Asn Ile Ile Gly Asp Ile Arg Lys Ala
            20                  25                  30

His Cys

Ala His Cys
        35

<210> SEQ ID NO 18
<211> LENGTH: 35
<212> TYPE: PRT
<213> ORGANISM: Artificial Sequence
<220> FEATURE:
<223> OTHER INFORMATION: synthetic HIV-1 envelope protein V3 loop region

<400> SEQUENCE: 18

Lys Cys Thr Arg Pro Gly Asn Ser Thr Arg Arg Gly Ile Leu Val Gly
 1               5                  10                  15

Thr Arg Arg Phe Tyr Thr Thr Arg Asn Ile Ile Gly Asp Ile Arg

```
Leu Cys Leu Phe Cys Tyr His Arg Leu Arg Asp Leu Leu Ile Val
            260                 265                 270

Ala Arg Ile Val Glu Leu Leu Gly His Arg Gly Trp Glu Ile Leu Lys
275                 280                 285

Tyr Trp Trp Asn Leu Leu Tyr Trp Ser Gln Glu Leu Lys Lys Ser
290                 295                 300

Ala Ile Ser Leu Phe Asn Ala Ile Ala Ile Val Ala Glu Gly Thr
305                 310                 315                 320

Asp Arg Ile Ile Glu Ile Ala Gln Arg Ala Phe Arg Ala Phe Leu His
            325                 330                 335

Ile Pro Arg Arg Ile Arg Gln Gly Phe Glu Arg Ala Leu Leu
            340                 345                 350

<210> SEQ ID NO 20
<211> LENGTH: 350
<212> TYPE: PRT
<213> ORGANISM: Human immunodeficiency virus 1
<220> FEATURE:
<223> OTHER INFORMATION: HIV-1 clones 13 and 21 gp41 envelope protein

<400> SEQUENCE: 20

Arg Glu Lys Arg Ala Ile Gly Gly Leu Gly Ala Leu Phe Leu Gly Phe
1               5                   10                  15

Leu Gly Ala Ala Gly Ser Ala Met Gly Ala Ala Ser Leu Thr Leu Thr
                20                  25                  30

Val Gln Ala Arg Gln Leu Leu Ser Gly Ile Val Gln Gln Gln Asn Asn
            35                  40                  45

Leu Leu Arg Ala Ile Glu Ala Gln Gln His Leu Leu Gln Leu Thr Val
50                  55                  60

Trp Gly Ile Lys Gln Leu Gln Ala Arg Val Leu Ala Val Glu Arg Tyr
65                  70                  75                  80

Leu Gln Asp Gln Gln Leu Leu Gly Ile Trp Gly Cys Ser Gly Lys Leu
                85                  90                  95

Ile Cys Thr Thr Asp Val Pro Trp Asn Thr Ser Trp Ser Asn Lys Ser
            100                 105                 110

Leu Asp Glu Ile Trp Asn Asn Met Thr Trp Met Gln Trp Asp Arg Glu
        115                 120                 125

Ile Asn Lys Tyr Thr Gly Ile Ile Tyr Thr Leu Ile Glu Asp Ser Gln
130                 135                 140

Ile Gln Gln Glu Lys Asn Glu Lys Glu Leu Leu Glu Leu Asp Lys Trp
145                 150                 155                 160

Ala Asn Leu Trp Asn Trp Phe Asn Ile Thr Asn Trp Leu Trp Tyr Ile
                165                 170                 175

Lys Ile Phe Ile Met Ile Val Ala Gly Leu Val Gly Leu Arg Ile Val
            180                 185                 190

Phe Ser Val Leu Ser Ile Val Asn Arg Val Arg Gln Gly Tyr Ser Pro
        195                 200                 205

Leu Ser Phe Gln Thr Arg Leu Pro Thr Pro Arg Gly Pro Asp Arg Pro
210                 215                 220

Glu Gly Thr Glu Glu Glu Gly Gly Glu Ser Gly Arg Asp Arg Ser Gly
225                 230                 235                 240

Pro Leu Val Asp Gly Phe Leu Ala Ile Ile Trp Val Asp Leu Arg Ser
                245                 250                 255

Leu Cys Leu Phe Ser Tyr His Arg Leu Arg Asp Leu Leu Ile Val
            260                 265                 270
```

-continued

```
Ala Arg Ile Val Glu Leu Leu Gly Arg Arg Gly Trp Glu Ser Leu Lys
        275                 280                 285

Tyr Trp Trp Asn Leu Leu Gln Tyr Trp Ser Gln Glu Leu Lys Lys Ser
290                 295                 300

Ala Ile Ser Leu Phe Asn Ala Ile Ala Ile Ala Val Ala Glu Gly Thr
305                 310                 315                 320

Asp Arg Ile Ile Glu Ile Ala Gln Arg Ala Phe Arg Ala Phe Leu His
                325                 330                 335

Ile Pro Arg Arg Ile Arg Gln Gly Phe Glu Arg Ala Leu Leu
                340                 345                 350

<210> SEQ ID NO 21
<211> LENGTH: 350
<212> TYPE: PRT
<213> ORGANISM: Human immunodeficiency virus 1
<220> FEATURE:
<223> OTHER INFORMATION: HIV-1 clones 14 and 86 gp41 envelope protein

<400> SEQUENCE: 21

Arg Glu Lys Arg Ala Ile Gly Val Leu Gly Ala Leu Phe Leu Gly Phe
1               5                   10                  15

Leu Gly Ala Ala Gly Ser Thr Met Gly Ala Ala Ser Leu Thr Leu Thr
                20                  25                  30

Val Gln Ala Arg Gln Leu Leu Ser Gly Ile Val Gln Gln Gln Asn Asn
            35                  40                  45

Leu Leu Arg Ala Ile Glu Ala Gln Gln His Leu Leu Gln Leu Thr Val
        50                  55                  60

Trp Gly Ile Lys Gln Leu Gln Ala Arg Val Leu Ala Val Glu Arg Tyr
65                  70                  75                  80

Leu Gln Asp Gln Gln Leu Leu Gly Ile Trp Gly Cys Ser Gly Lys Leu
                85                  90                  95

Ile Cys Thr Thr Ala Val Pro Trp Asn Thr Ser Trp Ser Asn Lys Ser
                100                 105                 110

Leu Asp Glu Ile Trp Asn Asn Met Thr Trp Met Gln Trp Asp Arg Glu
            115                 120                 125

Ile Asn Lys Tyr Asn Gly Ile Ile Tyr Thr Leu Ile Glu Glu Ser Gln
        130                 135                 140

Ile Gln Gln Asp Lys Asn Glu Lys Glu Leu Leu Glu Leu Asp Lys Trp
145                 150                 155                 160

Ala Asn Leu Trp Asn Trp Phe Asn Ile Thr Asn Trp Leu Trp Tyr Ile
                165                 170                 175

Lys Ile Phe Ile Ile Ile Val Ala Gly Leu Val Gly Leu Arg Ile Val
                180                 185                 190

Phe Ser Val Leu Ser Ile Val Asn Arg Val Arg Gln Gly Tyr Ser Pro
            195                 200                 205

Leu Ser Phe Gln Thr Arg Leu Pro Thr Pro Arg Gly Pro Asp Arg Pro
        210                 215                 220

Glu Gly Thr Glu Glu Glu Gly Gly Glu Ser Gly Arg Asp Arg Ser Glu
225                 230                 235                 240

Pro Leu Val Asp Gly Phe Leu Ala Ile Ile Trp Val Asp Leu Arg Ser
                245                 250                 255

Leu Cys Leu Phe Ser Tyr His Arg Leu Arg Asp Leu Leu Leu Ile Val
                260                 265                 270

Ala Arg Ile Val Glu Leu Leu Gly Arg Arg Gly Arg Glu Ile Leu Lys
        275                 280                 285

Tyr Trp Trp Asn Leu Leu Gln Tyr Trp Ser Gln Glu Leu Lys Lys Ser
```

-continued

```
            290                 295                 300
Ala Val Ser Leu Phe Asn Ala Ile Ala Ile Ala Val Ala Glu Gly Thr
305                 310                 315                 320

Asp Arg Ile Ile Glu Ile Ala Gln Arg Ala Phe Arg Ala Phe Leu His
                325                 330                 335

Ile Pro Arg Arg Ile Arg Gln Gly Phe Glu Arg Ala Leu Leu
                340                 345                 350
```

METHOD FOR DETERMINING HUMAN IMMUNODEFICIENCY VIRUS (HIV) CORECEPTOR UTILIZATION BY EXAMINING GP41 MOLECULAR DETERMINANTS

1. CROSS REFERENCE TO RELATED APPLICATIONS

This application is a U.S. National Stage application of International Application No. PCT/US2007/013874, filed 12 Jun. 2007, now expired, which claims the priority benefit of U.S. Patent Application No. 60/813,636 filed 13 Jun. 2006, now expired, the contents of which are incorporated herein by reference in their entirety.

This invention was supported in part by SBIR (Small Business Innovation Research) grant under grant number R44-A1048990 awarded by the National Institute of Health of the United States.

Throughout this application, various publications are referenced by author and date within the text. Full citations for these publications may be found listed alphabetically at the end of the specification immediately preceding the claims. All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

2. BACKGROUND

Enveloped animal viruses attach to and enter the host cell via the interaction of viral proteins in the virion membrane (envelope proteins) and cell surface proteins (virus receptors). Receptor recognition and binding are mediated by the surface envelope protein. Virus entry is an attractive target for anti-viral treatment; numerous drugs that are designed to block virus attachment or membrane fusion have been or are currently being evaluated in preclinical or clinical studies (Richman, 1998; PhRMA, 1999; Stephenson, 1999). For example, the attachment inhibitor SCH-D (vivriviroc), which blocks the interaction between viral membrane proteins of HIV-1 and the cellular co-receptor CCR5, is currently being evaluated in clinical studies for its effectiveness as an anti-viral treatment (Shurman, 2004). Other entry inhibitors currently under investigation include UK-427857 (maraviroc; Pfizer), TNX-355 (Tanox Inc.), AMD-070 (AnorMED), Pro 140 (Progenics), FP-21399 (EMD Lexigen), and BMS-488043 (Bristol-Myers Squibb). One entry inhibitor, T-20 (enfuvirtide; Roche/Trimeris), has been approved for treatment of HIV infection by the United States Food and Drug Administration.

As these drugs continue to be developed and enter the clinic, assays are needed that can rapidly and easily detect the emergence of viruses with reduced susceptibility to entry inhibitors. Also needed are methods to determine whether a virus can enter cells expressing particular co-receptors to determine whether inhibition of virus-co-receptor interactions might be useful in the treatment of infection. These and other unmet needs are provided by the present invention.

3. SUMMARY

In certain aspects, the invention provides a method for determining whether a human immunodeficiency virus ("HIV") is likely to have enhanced ability to enter a cell expressing CD4 and CXCR4 relative to a reference HIV, comprising detecting, in a nucleic acid encoding an envelope protein of the HIV, a codon encoding valine in a codon corresponding to codon 515 of HIV strain HXB2, a codon encoding valine in a codon corresponding to codon 539 of HIV strain HXB2, or a codon encoding alanine in a codon corresponding to codon 607 of HIV strain HXB2, wherein the presence of valine encoded in codon 515 or 539 or alanine encoded in codon 607 indicates that the HIV is likely to have enhanced ability to enter a cell expressing CD4 and CXCR4 relative to a reference HIV.

In certain embodiments, the reference HIV is NL4-3, HXB2, or SF2. In certain embodiments, the reference HIV has an envelope gene that encodes an envelope protein having a sequence identical to the envelope protein of the HIV except for one or more differences at a codon corresponding to codon 515, 539, or 607 of HIV strain HXB2.

In certain embodiments, the envelope protein comprises a valine at codon 515. In certain embodiments, the envelope protein comprises a valine at codon 539. In certain embodiments, the envelope protein comprises an alanine at codon 607. In certain embodiments, the envelope protein comprises a valine at codon 515, a valine at codon 539, and an alanine at codon 607.

In another aspect, the invention provides a method for determining whether an HIV is likely to have reduced ability to enter a cell expressing CD4 and CCR5 relative to a reference HIV, comprising detecting, in a nucleic acid encoding an envelope protein of the HIV, a codon encoding valine in a codon corresponding to codon 515 of HIV strain HXB2, a codon encoding valine in a codon corresponding to codon 539 of HIV strain HXB2, or a codon encoding alanine in a codon corresponding to codon 607 of HIV strain HXB2, wherein the presence of valine encoded in codon 515 or 539 or alanine encoded in codon 607 indicates that the HIV is likely to have reduced ability to enter a cell expressing CD4 and CCR5 relative to a reference HIV.

In certain embodiments, the reference HIV is NL4-3, HXB2, or SF2. In certain embodiments, the reference HIV has an envelope gene that encodes an envelope protein having a sequence identical to the envelope protein of the HIV except for one or more differences at a codon corresponding to codon 515, 539, or 607 of HIV strain HXB2.

In certain embodiments, the envelope protein comprises a valine at codon 515. In certain embodiments, the envelope protein comprises a valine at codon 539. In certain embodiments, the envelope protein comprises an alanine at codon 607. In certain embodiments, the envelope protein comprises a valine at codon 515, a valine at codon 539, and an alanine at codon 607.

4. BRIEF DESCRIPTION OF THE FIGURES

FIG. 1: Structure of Envelope Expression and Viral Expression Vectors.

FIG. 1A: The HIV envelope expression vector (pHIVenv) is modified to accept envelope sequences that have been amplified from subject plasma samples. The designations a/b and c/d, refer to restriction endonuclease sites positioned at the 5' and 3' end of the HIV-1 envelope polyprotein (gp160).

Figure 1B:
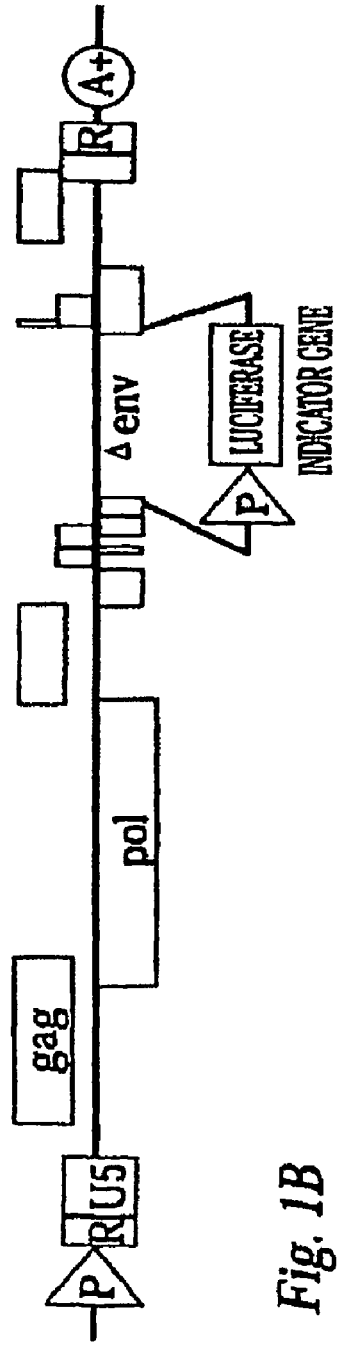

FIG. 1B: The HIV expression vector (pHIVlucΔU3) encodes all HIV proteins except the envelope polyprotein. A portion of the envelope gene has been deleted to accommodate an indicator gene cassette, in this case, firefly luciferase, that is used to monitor the ability of the virus to replicate in the presence or absence of anti-viral drugs. The 3' U3 region has been partially deleted to prevent transcription from the 5' LTR in infected cells. Virus produced in this system is limited to a single round of replication.

Figure 2A:
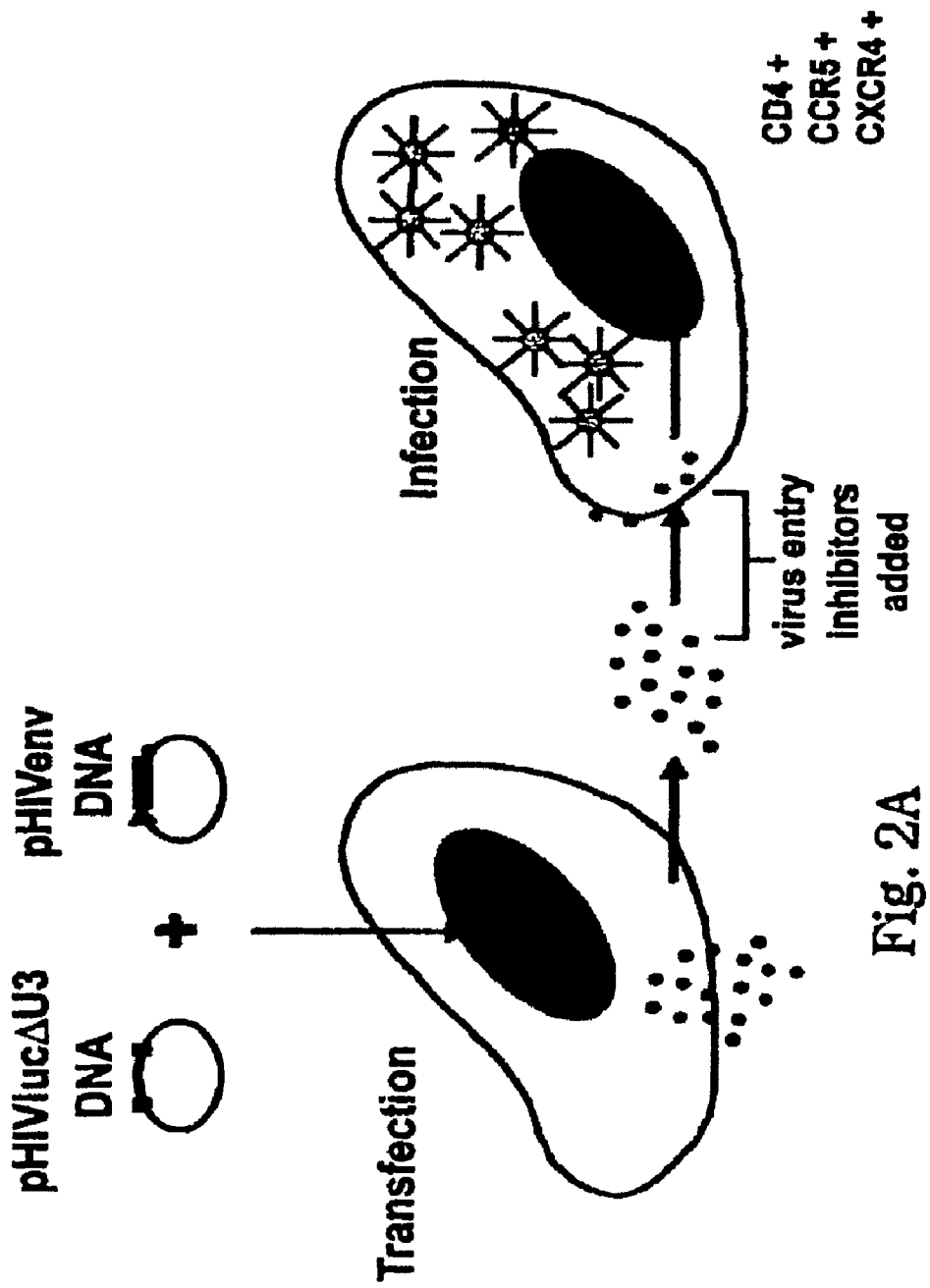

FIG. 2A: Cell Based Entry Assay

In this embodiment, drug susceptibility, co-receptor tropism and antibody-mediated virus neutralization testing are performed by co-transfecting a host cell with pHIVenv and pHIVlucΔU3. The host cell produces HIV particles that are pseudo-typed with HIV envelope sequences derived from the test virus or subject sample. Virus particles are collected (~48 h) after transfection and are used to infect target cells that express HIV receptors (e.g. CD4) and co-receptors (e.g. CXCR4, CCR5). After infection (~72 h) the target cells are lysed and luciferase activity is measured. HIV must complete one round of replication to successfully infect the target host cell and produce luciferase activity. If the virus is unable to enter the target cell, luciferase activity is diminished. This system can be used to evaluate susceptibility to entry inhibitors, receptor and co-receptor tropism, and virus neutralization.

Figure 2B:
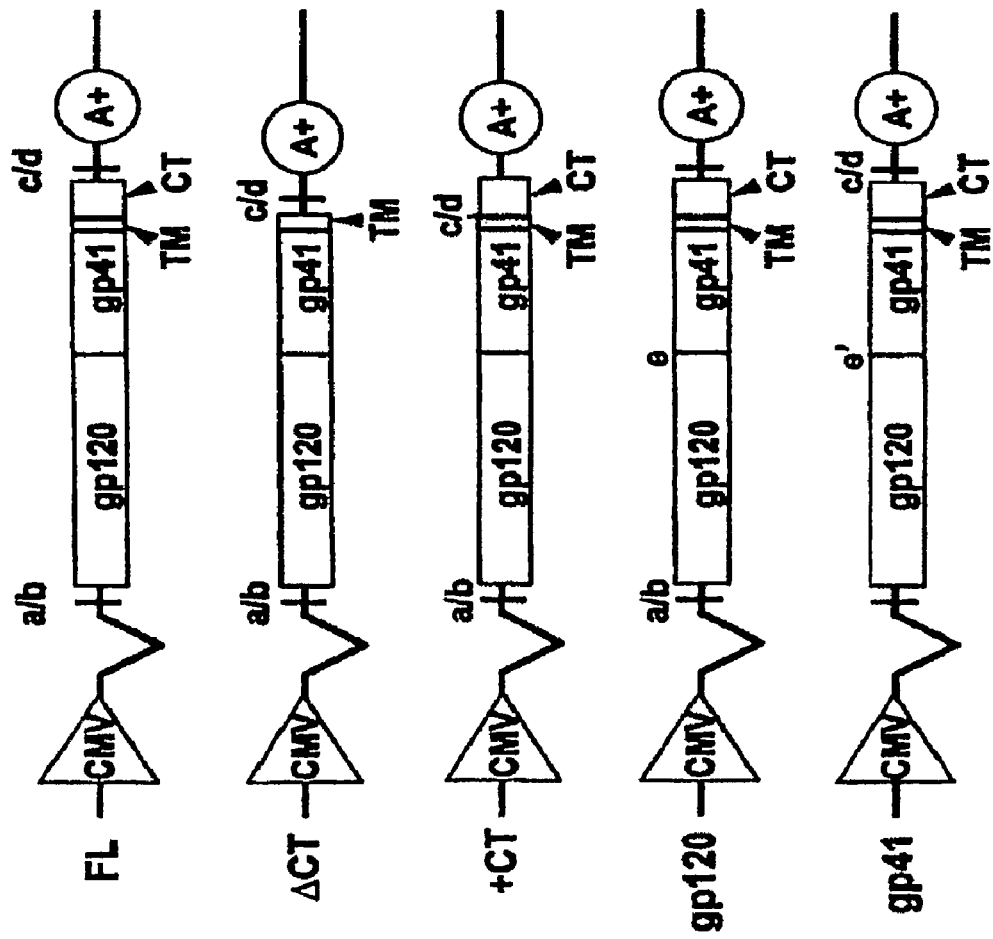

FIG. 2B: HIV Envelope Expression Vectors.

HIV envelope sequences are amplified from subject samples and inserted into expression vectors using restriction endonuclease sites (5' a/b and 3'c/d). Envelope transcription is driven by the immediate early gene promoter of human cytomegalovirus (CMV). Envelope RNA is polyadenylated using an simian virus 40 (SV40) polyadenylation signal sequence (A+). An intron located between the CMV promoter and the HIV envelope sequences is designed to increase envelope mRNA levels in transfected cells. FL-express full-length envelope proteins (gp120, gp41); "ACT"-express envelope proteins (gp120, gp21) lacking the C-terminal cytoplasmic tail domain of gp41; "+CT"-express envelope proteins (gp120, gp41) containing a constant pre-defined gp41 cytoplasmic tail domain; "gp120-"-express gp120 proteins derived from the subject together with a constant pre-defined gp41; and "gp41-"-express a constant pre-defined gp120 together with gp41 proteins derived from the subject.

Figure 3A:
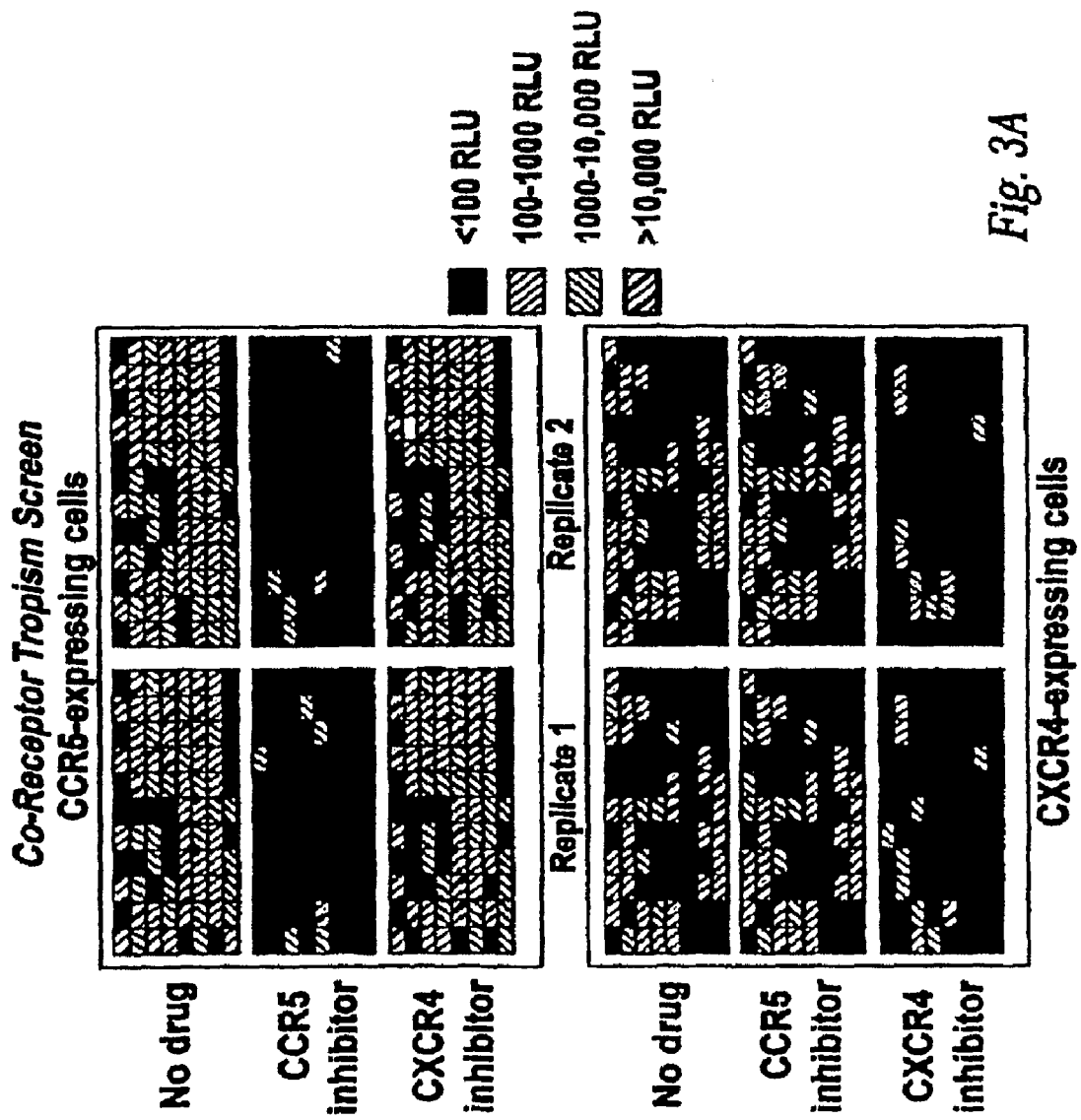

FIG. 3A: Co-Receptor Tropism Screening Assay.

In this figure, the assay is performed using two cell lines. One cell line expresses CD4 and CCR5 (top six panels). The other cell line expresses CD4 and CXCR4 (bottom six panels). The assay is performed by infecting cells with a large number of recombinant virus stocks derived from cells transfected with pHIVenv and pHIVlucΔU3 vectors. The example shown represents the analysis of 96 viruses formatted in a 96 well plate infections are performed in the absence of drug (no drug), or in the presence of a drug that preferentially inhibits either R5 tropic (CCR inhibitor) or X4 tropic (CXCR4 inhibitor) viruses. Co-receptor tropism is assessed by comparing the amount of luciferase activity produced in each cell type, both in the presence and absence of drug (see FIG. 3B for interpretation of assay results).

Figure 3B:
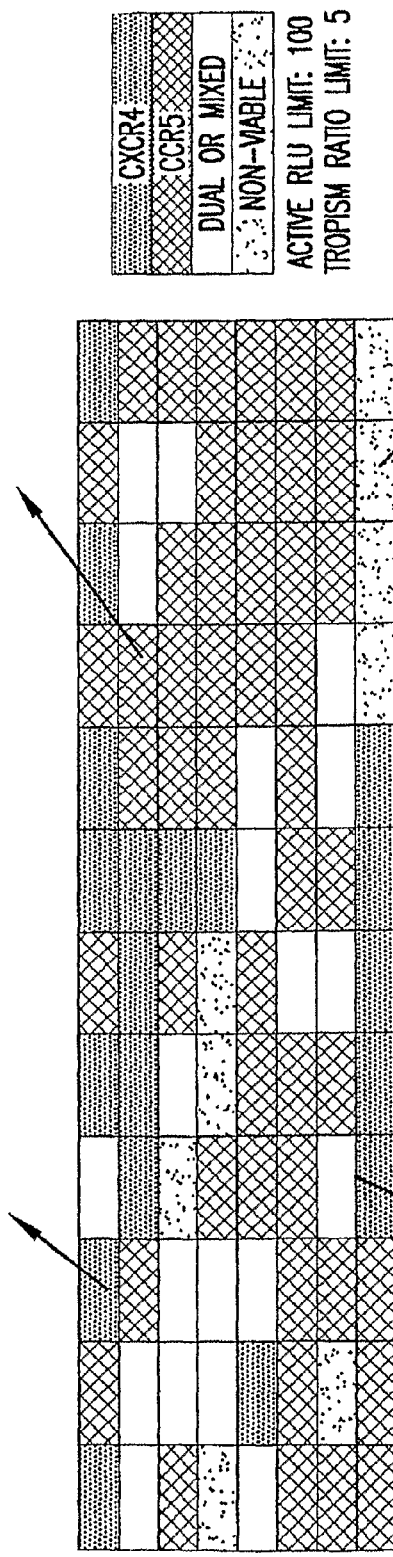

FIG. 3B: Determining Co-Receptor Tropism.

In this figure, the results of the assay are interpreted by comparing the ability of each sample virus to infect (produce luciferase activity) in cells expressing CD4/CCR5 (R5 cells) or cells expressing CD4/CXCR4 (X4 cells). The ability of a CCR5 or CXCR4 inhibitor to specifically block infection (inhibit luciferase activity) is also evaluated. X4 tropic viruses infect X4 cells but not R5 cells. Infection of X4 cells is blocked by the CXCR4 inhibitor. R5 tropic viruses infect R5 cells but not X4 cells. Infection of R5 cells is blocked by the CCR5 inhibitor. Dual tropic or X4/R5 mixtures infect X4 and R5 cells. Infection of R5 cells is blocked by the CCR5 inhibitor and infection of X4 cells is blocked by the CXCR4 inhibitor. Non-viable viruses do not replicate in either X4 or R5 cells.

FIG. 4A: Measuring Entry Inhibitor susceptibility: Fusion Inhibitor.

In this figure, susceptibility to the fusion inhibitor T-20 is demonstrated. Cells expressing CD4, CCR5 and CXCR4 were infected in the absence of T-20 and over a wide range of T-20 concentrations α-axis log 10 scale). The percent inhibition of viral replication (y-axis) was determined by comparing the amount of luciferase produced in infected cells in the presence of T-20 to the amount of luciferase produced in the absence of T-20. R5 tropic, X4 tropic and dual tropic viruses were tested. Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. NL4-3: well-characterized X4 tropic strain; JRCSF: well-characterized R5 tropic strain; 91US005.11: R5 tropic isolate obtained from the NIH AIDS Research and Reference Reagent Program (ARRRP); 92HT593.1: Dual tropic (X4R5) isolate obtained from the NIH ARRRP; and 92HT599.24: X4 tropic isolate obtained from the NIH ARRRP.

Figure 4B:
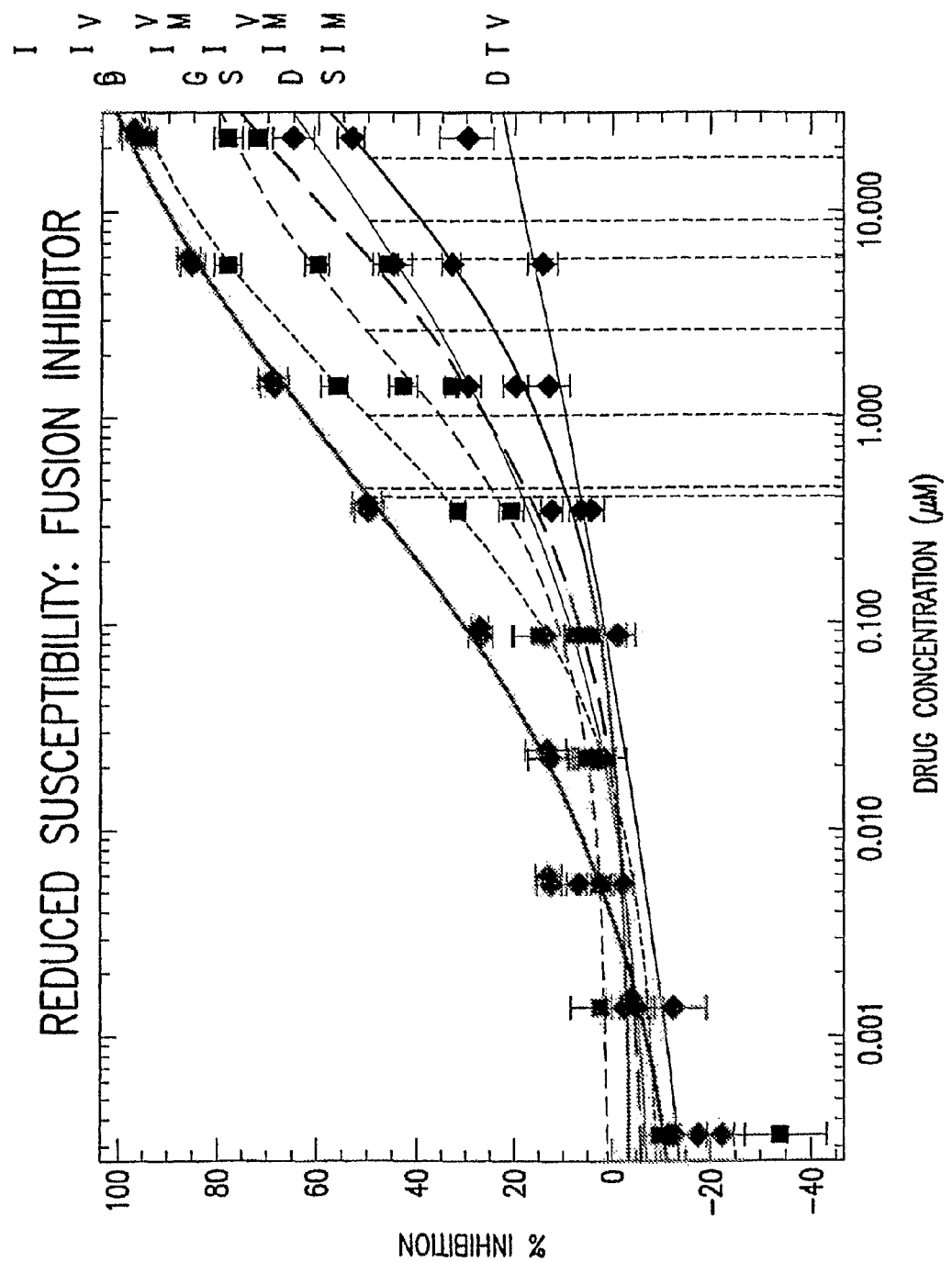

FIG. 4B: Measuring Entry Inhibitor Susceptibility: Drug Resistance Mutations.

In this figure, reduced susceptibility to the fusion inhibitor T-20 conferred by specific mutations in the gp41 envelope protein is demonstrated. Cells expressing CD4, CCR5 and CXCR4 were infected in the absence of T-20 and over a wide range of T-20 concentrations (x-axis log 10 scale). The percent inhibition of viral replication (y-axis) was determined by comparing the amount of luciferase produced in infected cells in the presence of T-20 to the amount of luciferase produced in the absence of T-20. Isogenic viruses containing one or two specific mutations in the gp41 transmembrane envelope protein were tested (highlighted in red in the figure legend). Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. No mutation (wild type sequence): GIV; Single mutations: GIV, DIM, SIV; Double mutations: DIM, SIM, DTV.

Figure 5:
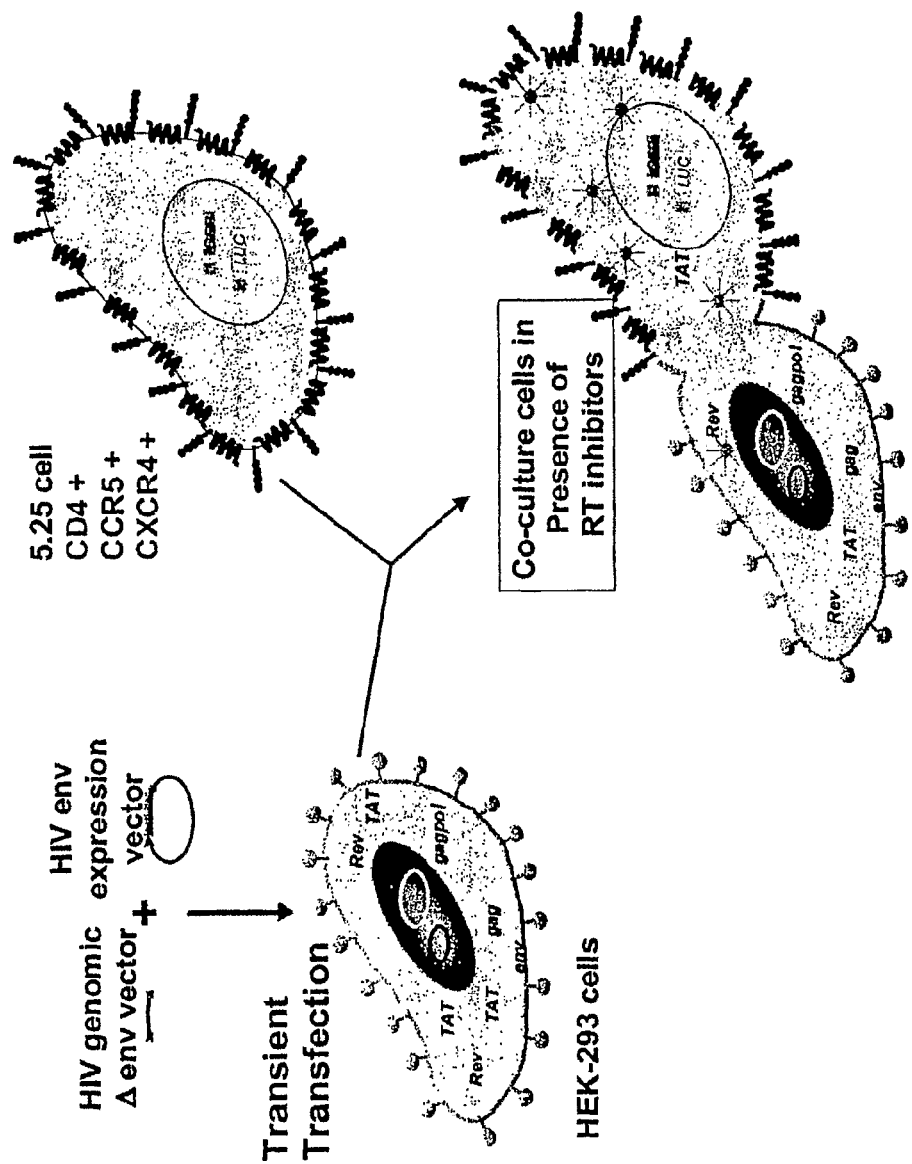

FIG. 5: Fusogenicity Assay

FIG. 5 presents a diagrammatic representation of a fusogenicity assay performed to assess the fisogenic activity of HIV envelope proteins.

Figure 6:
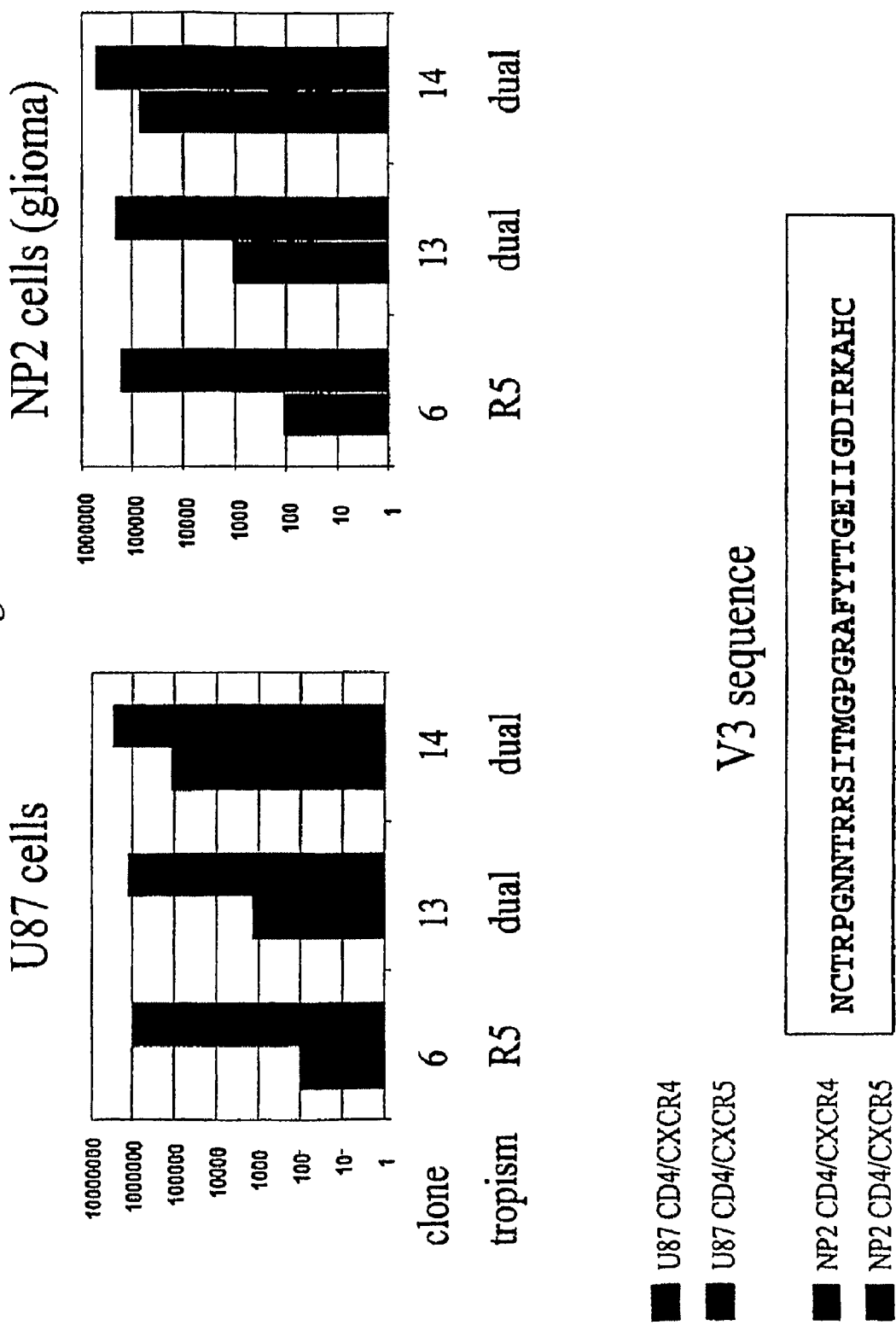

FIG. 6: Tropism Assay with Different Cell Lines

FIG. 6 presents a graphical representation comparing entry into two different cell lines expressing CD4 and either CCR5 or CXCR4. As shown in FIG. 6, relative activity was consistent in both U87 cells and NP2 cells expressing appropriate receptors and co-receptors. V3 sequence=SEQ ID NO:15.

Figure 7:
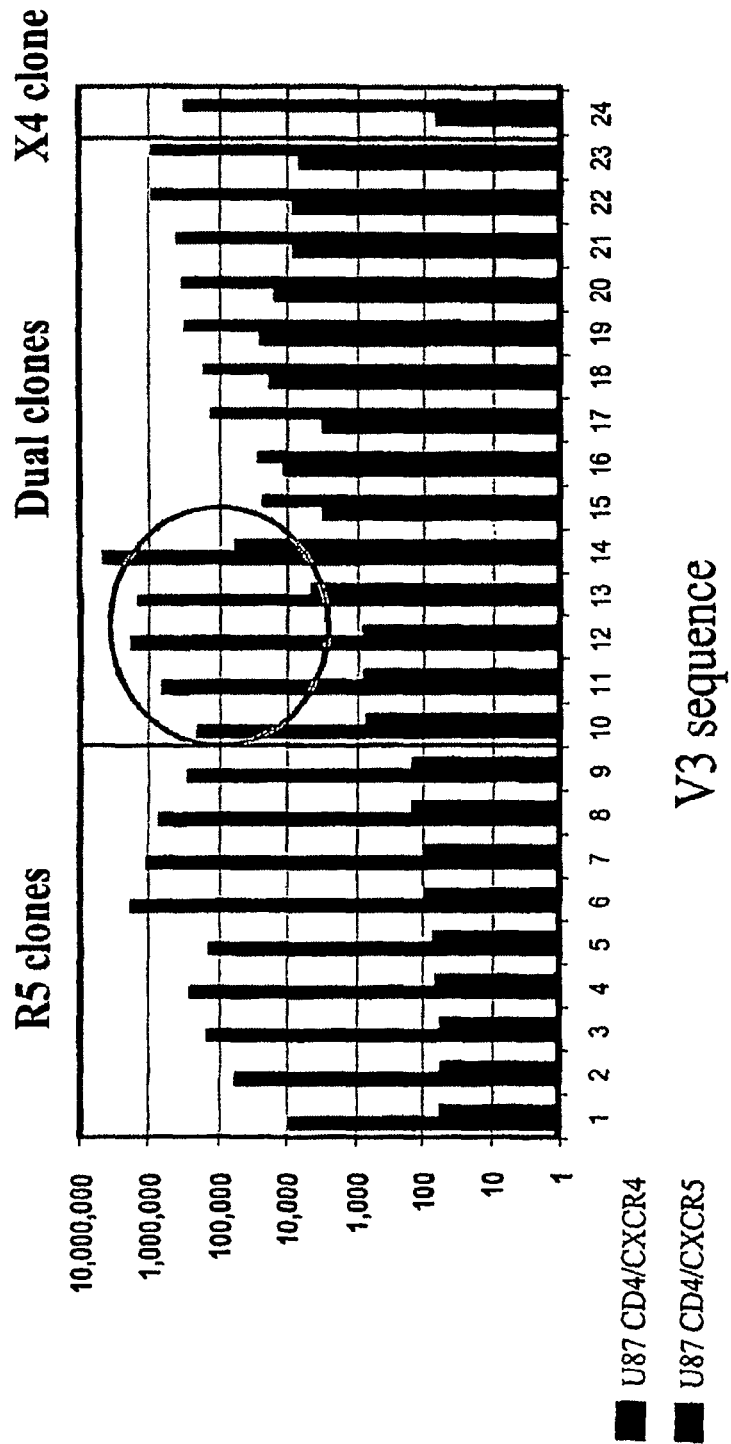

FIG. 7: Distribution of Ability to Enter Using CCR5 or CXCR4 as Co-Receptor Among 24 Clones Isolated from a Single Patient FIG. 7 presents a graphical representation quantifying entry into U87 cells expressing CD4 and either CCR5 or CXCR4 mediated by 24 individual envelope protein clones isolated from a single patient. V3 sequences=SEQ ID NOS: 15, 15, 16-18, respectively.

Figure 8:
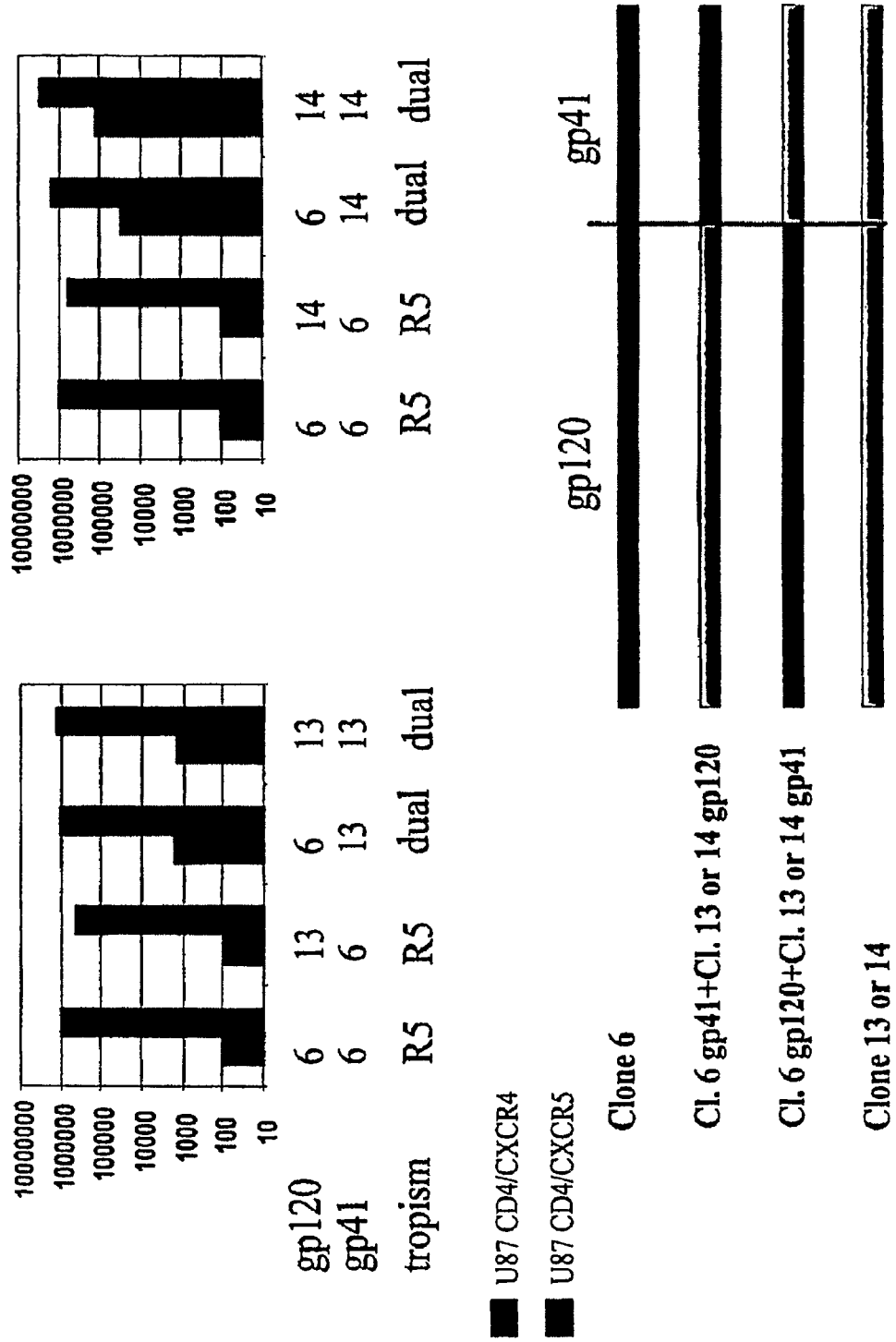

FIG. 8: Mapping of Determinants for CXCR4-Mediated Entry to gp41.

FIG. 8 presents a graphical representation of the ability of HIV viral particles comprising chimeric envelope proteins to enter U87 cells expressing CD4 and either CCR5 or CXCR4.

Figure 9:
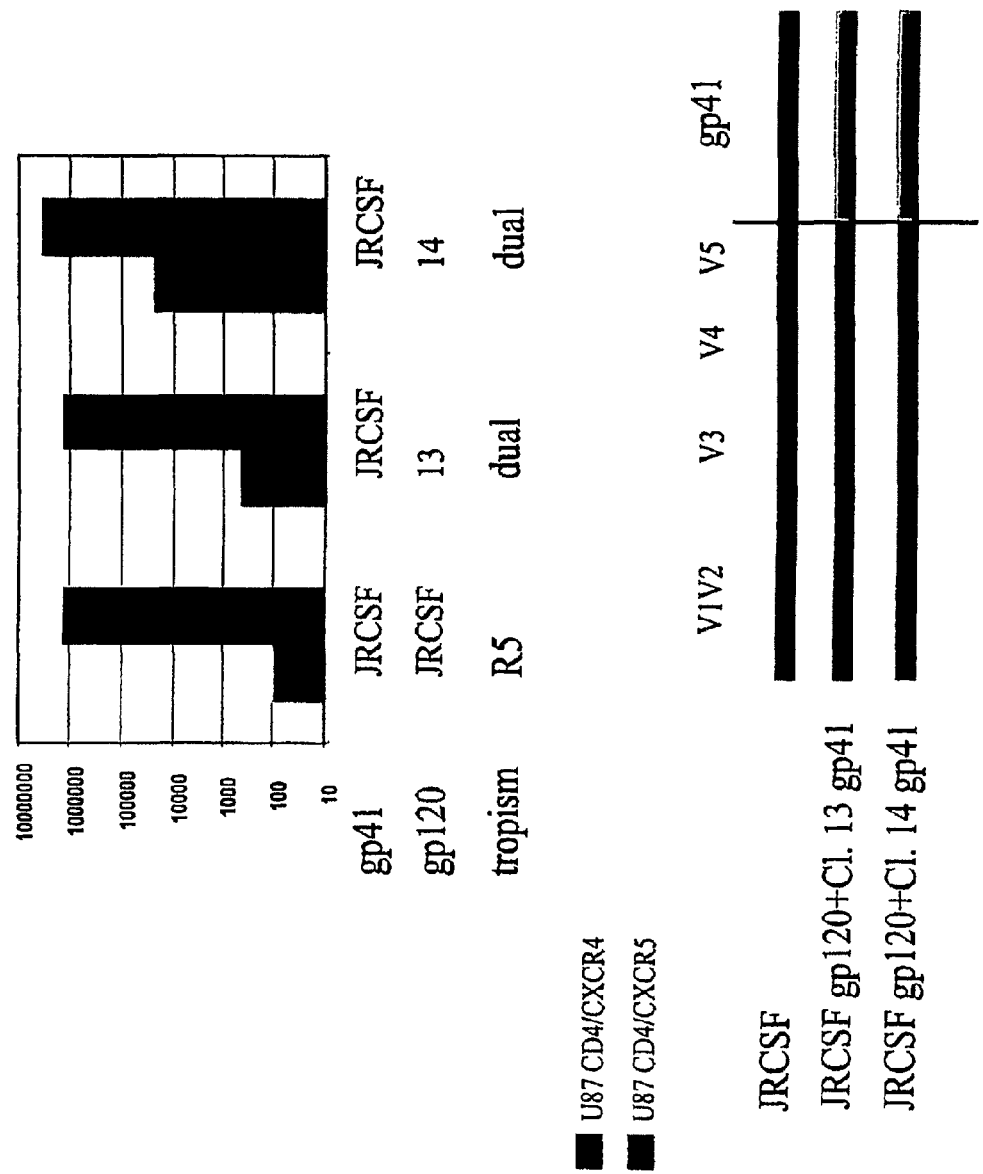

FIG. 9: Mapping of Determinants for CXCR4-Mediated Entry to gp41.

FIG. 9 presents a graphical representation of the ability of HIV viral particles comprising chimeric envelope proteins to enter U87 cells expressing CD4 and either CCR5 or CXCR4.

Figure 10:
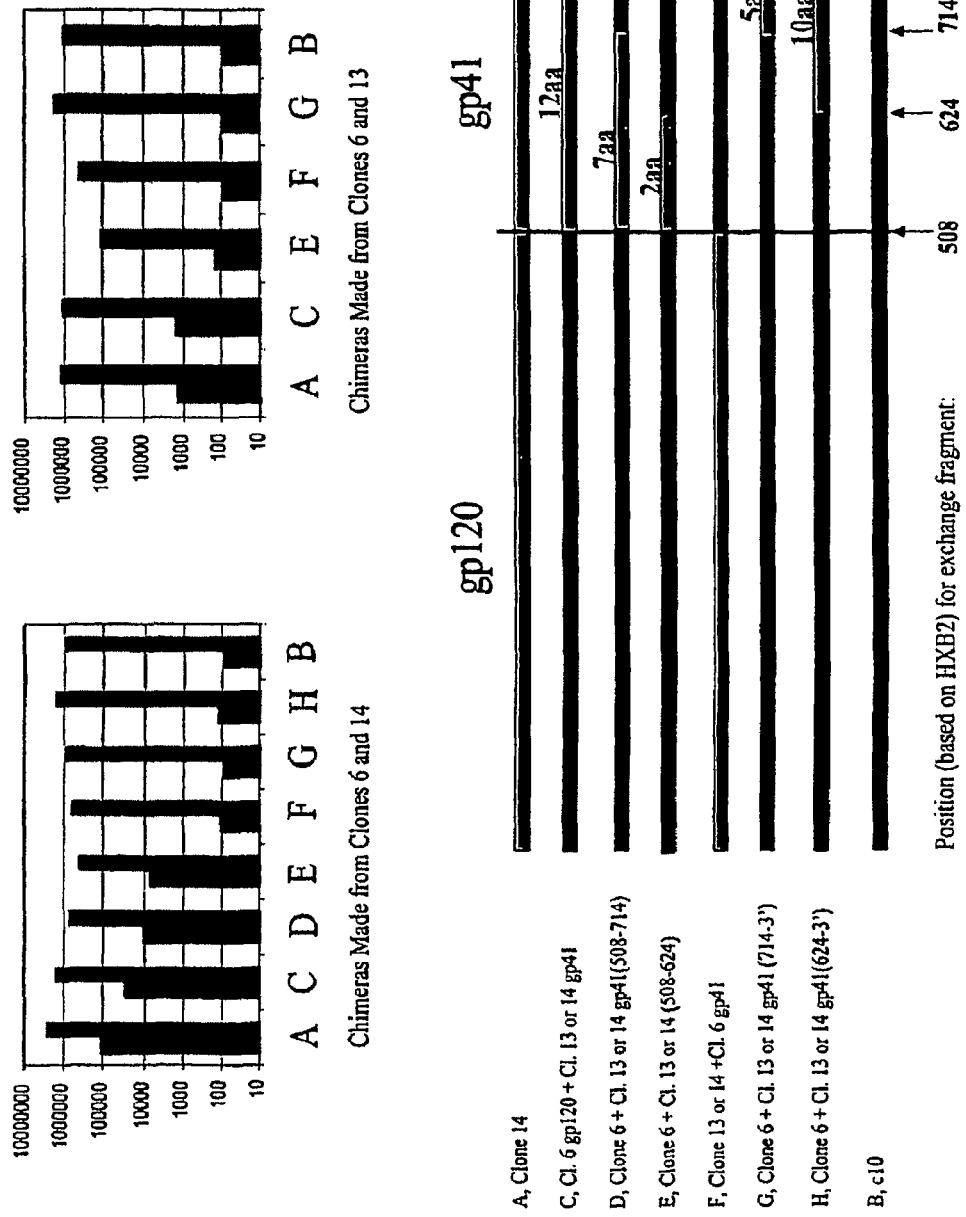

FIG. 10: Mapping of Determinants for CXCR4-Mediated Entry to gp41.

FIG. 10 presents a graphical representation of the ability of HIV viral particles comprising chimeric envelope proteins to enter U87 cells expressing CD4 and either CCR5 or CXCR4, where the chimeric proteins have a modified gp41.

Figure 11:
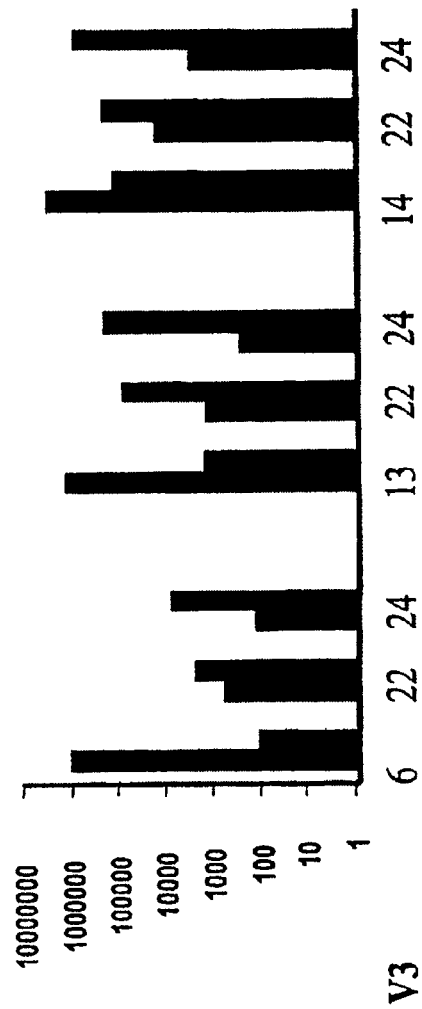

FIG. 11: Interactions Between Variable Region 3 and gp41 on CXCR4-Mediated Entry.

FIG. 11 presents a graphical representation of the ability of HIV viral particles comprising chimeric envelope proteins to enter U87 cells expressing CD4 and either CCR5 or CXCR4, where the chimeric proteins have a modified V3 region. V3 sequences=SEQ ID NOS:15, 16, 17, 15, 16, 17, 15, 16, 17, respectively.

FIG. 12: Alignment of gp41 Sequences from Three Individual Patient Clones.

FIG. 12 presents an alignment of the amino acid sequences of three individual patient clones (SEQ ID NOS:19-21) having different abilities to enter cells expressing CD4 and either CCR5 or CXCR4.

FIG. 13: Reduced Susceptibility to Co-Receptor Inhibitors Maps to gp41

FIG. 13 presents log-sigmoid curves showing the sensitivity or resistance to CCR5 and CXCR4 for individual patient envelope clones and for chimeric envelope proteins made from individual patient clones, showing that resistance to both CCR5 and CXCR4 inhibitors maps to the gp41 protein.

FIG. 14: Phylogenetic Analysis of gp160 env Sequences

FIG. 14 presents a phylogentic analysis of gp160 env sequences of env clones isolated from a patient plasma sample.

FIG. 15: Effect of env Sequences Outside of V3 Regions on Viral Tropism

FIG. 15 presents a graphical representation of the ability of HIV viral particles comprising chimeric envelope proteins to enter U87 cells expressing CD4 and either CCR5 or CXCR4. V3 sequences=SEQ ID NOS:11, 11, 12, 12, 11, 11, 13, 13, 11, 11, 14, 14, respectively.

FIG. 16: Effect of env Sequences Outside of V3 Regions on Viral Tropism

FIG. 16 presents a graphical representation of the ability of HIV viral particles comprising chimeric envelope proteins to enter U87 cells expressing CD4 and either CCR5 or CXCR4. V3 sequences=SEQ ID NOS:11, 11, 11, 12, 12, 12, 12, 14, 14, 14, 14, respectively.

FIG. 17: Mapping of Determinants for CXCR4-Mediated Entry to gp41.

FIG. 17 presents a graphical representation of the ability of HIV viral particles comprising chimeric envelope proteins to enter U87 cells expressing CD4 and either CCR5 or CXCR4.

FIG. 18: Fine Mapping of Determinants for CXCR4-Mediated Entry to gp41.

FIG. 18 presents a graphical representation of the ability of HIV viral particles comprising chimeric envelope proteins to enter U87 cells expressing CD4 and either CCR5 or CXCR4.

FIG. 19: Alignment of gp41 Sequences from Three Individual Patient Clones.

FIG. 19 presents an alignment of the amino acid sequences of three individual patient clones (SEQ ID NOS:19-21) having different abilities to enter cells expressing CD4 and either CCR5 or CXCR4.

5. DEFINITIONS

As used herein, the following terms shall have the following meanings:

A "phenotypic assay" is a test that measures a phenotype of a particular virus, such as, for example, HIV, or a population of viruses, such as, for example, the population of HIV infecting a subject. The phenotypes that can be measured include, but are not limited to, the resistance or susceptibility of a virus, or of a population of viruses, to a specific anti-viral agent, or that measures the replication capacity of a virus.

A "genotypic assay" is an assay that determines a genotype of an organism, a part of an organism, a population of organisms, a gene, a part of a gene, or a population of genes. Typically, a genotypic assay involves determination of the nucleic acid sequence of the relevant gene or genes. Such assays are frequently performed in HIV to establish, for example, whether certain mutations are associated with drug resistance or susceptibility or altered replication capacity are present.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.,* 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-X program, operated with default parameters, including an open gap penalty of 10:0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease or reverse transcriptase is the protease or reverse transcriptase coding sequence, respectively, present in NL4-3 HIV (GenBank Accession No. AF324493). Likewise, the reference protease or reverse transcriptase is that encoded by the NL4-3 HIV sequence. For embodiments of the invention comprising HIV envelope, the reference nucleic acid encoding envelope is the envelope coding sequence present in HXB2 HIV (GenBank Accession No. AAB50262). Likewise, the reference envelope is that encoded by the HXB2 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, *Methods in Enzymology* 65:499), dideoxy sequencing (Sanger et al., 1977, *Proc. Natl. Acad. Sci. USA* 74:5463) or hybridization-based approaches (see e.g., Sambrook et al., 2001, *Molecular Cloning: A Laboratory Manual*, Cold Spring Harbor Laboratory, 3rd ed., NY; and Ausubel et al., 1989, *Current Protocols in Molecular Biology*, Greene Publishing Associates and Wiley Interscience, NY).

A "mutant" is a virus, gene or protein having a sequence that has one or more changes relative to a reference virus, gene or protein.

The terms "peptide," "polypeptide" and "protein" are used interchangeably throughout.

The term "wild-type" refers to a reference virus that does not comprise a mutation known to be associated with a phenotype of interest.

The terms "polynucleotide," "oligonucleotide" and "nucleic acid" are used interchangeably throughout.

As used herein, a "glycosylation site" refers to a single amino acid or a specific sequence of amino acids that is recognized by one skilled in the art as being suitable for glycosylation as well as a single amino acid or a specific sequence of amino acids that is actually glycosylated.

6. DETAILED DESCRIPTION OF THE INVENTION

In certain aspects, the invention provides methods for determining whether an HIV is likely to have an enhanced ability to enter a cell expressing CD4 and CXCR4. The method comprises detecting, in a nucleic acid encoding an envelope protein of the HIV, the presence of one or more codons that are indicative of enhanced ability to enter a cell expressing CD4 and CXCR4 relative to a reference HIV. Exemplary codons are a codon encoding valine in a codon corresponding to codon 515 of HIV strain HXB2, a codon encoding valine in a codon corresponding to codon 539 of HIV strain HXB2, a codon encoding alanine in a codon corresponding to codon 607 of HIV strain HXB2 a codon encoding alanine in a codon corresponding to codon 529 of HIV strain HXB2, a codon encoding serine in a codon corresponding to codon 767 of HIV strain HXB2, a codon encoding arginine in a codon corresponding to codon 787 of HIV strain HXB2, a codon encoding serine in a codon corresponding to codon 792 of HIV strain HXB2, and any combination of two, three, four, five, six or seven of such codons.

The methods are useful, for example, to guide therapeutic decisions in treatment of subjects infected with HIV, whether newly infected or failing treatment, for screening compounds to identify compounds that will affect viruses resistant to other entry inhibitors, and to test whether anti-HIV antibodies can neutralize infection by a broad range of HIV that may be resistant to other strategies for treating and/or preventing HIV infection. Other uses of such methods will be apparent to those of skill in the art.

6.1 Methods for Determining Whether an HIV or HIV Population has an Enhanced Ability to Enter Cells Expressing CD4 and CXCR4

In one aspect, the invention provides methods for determining whether an HIV is likely to have an enhanced ability to enter a cell expressing CD4 and CXCR4. In certain aspects, the invention provides a method for determining whether an HIV is likely to have enhanced ability to enter a cell expressing CD4 and CXCR4 relative to a reference HIV, comprising detecting, in a nucleic acid encoding an envelope protein of the HIV, a codon encoding valine in a codon corresponding to codon 515 of HIV strain HXB2, a codon encoding valine in a codon corresponding to codon 539 of HIV strain HXB2, or a codon encoding alanine in a codon corresponding to codon 607 of HIV strain HXB2, wherein the presence of valine encoded in codon 515 or 539 or alanine encoded in codon 607 indicates that the HIV is likely to have enhanced ability to enter a cell expressing CD4 and CXCR4 relative to a reference HIV.

In certain embodiments, the reference HIV is NL4-3, HXB2, or SF2. In certain embodiments, the reference HIV has an envelope gene that encodes an envelope protein having a sequence identical to the envelope protein of the HIV except for one or more differences at a codon corresponding to codon 515, 539, or 607 of HIV strain HXB2. In certain embodiments, the envelope protein comprises a valine at codon 515. In certain embodiments, the envelope protein comprises a valine at codon 539. In certain embodiments, the envelope protein comprises an alanine at codon 607. In certain embodiments, the envelope protein comprises a valine at codon 515 and a valine at codon 539. In certain embodiments, the envelope protein comprises a valine at codon 515 and an alanine at codon 607. In certain embodiments, the envelope protein comprises a valine at codon 515, a valine at codon 539, and an alanine at codon 607.

In certain embodiments, the HIV's ability to enter a cell expressing CD4 and CXCR4 is increased at least about 2-fold. In certain embodiments, the HIV's ability to enter a cell expressing CD4 and CXCR4 is increased at least about 3-fold. In certain embodiments, the HIV's ability to enter a cell expressing CD4 and CXCR4 is increased at least about 4-fold. In certain embodiments, the HIV's ability to enter a cell expressing CD4 and CXCR4 is increased at least about 5-fold. In certain embodiments, the HIV's ability to enter a cell expressing CD4 and CXCR4 is increased at least about 6-fold. In certain embodiments, the HIV's ability to enter a cell expressing CD4 and CXCR4 is increased at least about 7-fold. In certain embodiments, the HIV's ability to enter a cell expressing CD4 and CXCR4 is increased at least about 8-fold. In certain embodiments, the HIV's ability to enter a cell expressing CD4 and CXCR4 is increased at least about 9-fold. In certain embodiments, the HIV's ability to enter a cell expressing CD4 and CXCR4 is increased at least about 10-fold. In certain embodiments, the HIV's ability to enter a cell expressing CD4 and CXCR4 is increased at least about 20-fold. In certain embodiments, the HIV's ability to enter a cell expressing CD4 and CXCR4 is increased at least about 40-fold. In certain embodiments, the HIV's ability to enter a cell expressing CD4 and CXCR4 is increased at least about 50-fold. In certain embodiments, the HIV's ability to enter a cell expressing CD4 and CXCR4 is increased at least about 100-fold.

In certain embodiments, the HIV's ability to enter a cell expressing CD4 and CXCR4 is increased at least about 10%. In certain embodiments, the HIV's ability to enter a cell expressing CD4 and CXCR4 is increased at least about 20%. In certain embodiments, the HIV's ability to enter a cell expressing CD4 and CXCR4 is increased at least about 30%. In certain embodiments, the HIV's ability to enter a cell expressing CD4 and CXCR4 is increased at least about 40%. In certain embodiments, the HIV's ability to enter a cell expressing CD4 and CXCR4 is increased at least about 50%. In certain embodiments, the HIV's ability to enter a cell expressing CD4 and CXCR4 is increased at least about 60%. In certain embodiments, the HIV's ability to enter a cell expressing CD4 and CXCR4 is increased at least about 70%. In certain embodiments, the HIV's ability to enter a cell expressing CD4 and CXCR4 is increased at least about 80%. In certain embodiments, the HIV's ability to enter a cell expressing CD4 and CXCR4 is increased at least about 90%.

The invention provides a method for determining whether a virus has developed an enhanced ability to enter a cell expressing CD4 and CXCR4 relative to a reference HIV which comprises: (a) determining whether a virus has an enhanced ability to enter a cell expressing CD4 and CXCR4 relative to a reference HIV according to a method of the invention, wherein a nucleic acid encoding a viral envelope protein is obtained from a subject at a first time; (b) determining whether a virus has an enhanced ability to enter a cell expressing CD4 and CXCR4 relative to a reference HIV according a method of the invention, wherein the nucleic acid encoding the viral envelope protein is obtained from the subject at a later second time; and (c) comparing the abilities determined in steps (a) and (b), wherein a increase in ability to enter a cell expressing CD4 and CXCR4 at the later second time indicates that the virus has developed an enhanced ability to enter the cell. In a particular embodiment, the subject has undergone or is undergoing anti-HIV therapy comprising an entry inhibitor, e.g., a CD4 inhibitor, a CCR5 inhibitor or a CXCR4 inhibitor.

In certain embodiments, this invention further provides a method for using virus entry inhibitor susceptibility to guide the treatment of subjects failing antiretroviral drug treatment.

In certain embodiments, this invention further provides methods for using virus entry inhibitor susceptibility to guide the treatment of subjects newly infected with HIV-1.

In another aspect, the methods comprise determining that a subject is infected with an HIV that has an enhanced ability to enter a cell expressing CD4 and CXCR4 relative to a reference HIV according to a method of the invention, then advising a medical professional of the treatment option of administering to the subject a therapeutic regimen that includes an HIV entry inhibitor. In certain embodiments, the HIV entry inhibitor is PRO 542, TNX-355, mAb B12, or mAb B4. In certain embodiments, the entry inhibitor is selected from the group consisting of BMS-488-403, PRO 542, mAb B4, mAb B12, TNX-355, UK-427857, SCH-D, GW-873140, AMD-11070, TAK-220, Pro-140, and mAb004. In certain embodiments, the entry inhibitor is selected from the group consisting of TNX-355, UK-427857, SCH-D, GW-873140, AMD-11070, and TAK-220. In certain embodiments, the entry inhibitor is selected from the group consisting of TNX-355, UK-427857, SCH-D, GW-873140, and TAK-220.

In still another aspect, the methods comprise determining that a subject is infected with an HIV that has an enhanced ability to enter a cell expressing CD4 and CXCR4 relative to a reference HIV according to a method of the invention, and administering to the subject a combination of anti-HIV agents that comprises an HIV entry inhibitor. In certain embodiments, the HIV entry inhibitor is PRO 542, TNX-355, mAb B12, or mAb B4. In certain embodiments, the entry inhibitor is selected from the group consisting of BMS-488-403, PRO 542, mAb B4, mAb B12, TNX-355, UK-427857, SCH-D, GW-873140, AMD-11070, TAK-220, Pro-140, and mAb004. In certain embodiments, the entry inhibitor is selected from the group consisting of TNX-355, UK-427857, SCH-D, GW-873140, AMD-11070, and TAK-220. In certain embodiments, the entry inhibitor is selected from the group consisting of TNX-355, UK-427857, SCH-D, GW-873140, and TAK-220.

In still another aspect, the methods comprise determining that a subject is infected with an HIV that is likely to have an enhanced ability to enter a cell expressing CD4 and CXCR4 relative to a reference HIV than a reference HIV according to a method of the invention, then advising a medical professional of the treatment option of administering to the subject a combination of anti-HIV agents that comprises an effective amount of an HIV entry inhibitor. In certain embodiments, the HIV entry inhibitor is PRO 542, TNX-355, mAb B12, or mAb B4. In certain embodiments, the entry inhibitor is selected from the group consisting of BMS-488,403, PRO 542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427, 857, SCH-D, GW-873,140, AMD-11070, and TAK-220. In certain embodiments, the entry inhibitor is selected from the group consisting of TNX-355, UK-427,857, SCH-D, GW-873,140, and TAK-220.

In yet another aspect, the methods comprise determining whether a subject is infected with an HIV that is likely to have an enhanced ability to enter a cell expressing CD4 and CXCR4 relative to a reference HIV according to a method of the invention at a first time, then determining whether the subject remains infected with an HIV that is likely to be have an enhanced ability to enter a cell expressing CD4 and CXCR4 relative to a reference HIV according to a method of the invention at a later second time.

6.2 Determining Viral Genotypes

As described herein, the present invention provides specific HIV envelope amino acid residues associated with enhanced ability to enter cells expressing CD4 and CXCR4 relative to a reference HIV. The sequences of HIV envelope proteins can be determined by any means known in the art for determining such sequences. For example, the envelope protein sequences can be determined from the viral gene that encodes a particular protein, or from the protein itself, i.e., in the amino acid sequence of the protein.

Nucleic acid sequences encoding envelope proteins having residues associated with enhanced ability to enter a cell expressing CD4 and CXCR4 can be detected by utilizing any suitable technique known to one of skill in the art without limitation. Viral DNA or RNA can be used as the starting point for such assay techniques, and may be isolated according to standard procedures which are well known to those of skill in the art.

The determination of specific nucleic acid sequences, such as in a particular region of the env gene, can be accomplished by a variety of methods including, but not limited to, restriction-fragment-length-polymorpbism detection based on allele-specific restriction-endonuclease cleavage (Kan and Dozy, 1978, *Lancet* ii:910-912), mismatch-repair detection (Faham and Cox, 1995, *Genome Res* 5:474-482), binding of MutS protein (Wagner et al., 1995, *Nucl Acids Res* 23:3944-3948), denaturing-gradient gel electrophoresis (Fisher et al., 1983, *Proc. Natl. Acad. Sci. U.S.A.* 80:1579-83), single-strand-conformation-polymorphism detection (Orita et al., 1983, *Genomics* 5:874-879), RNAase cleavage at mismatched base-pairs (Myers et al., 1985, *Science* 230:1242), chemical (Cotton et al., 1988, *Proc. Natl. Acad. Sci. USA.* 85:4397-4401) or enzymatic (Youil et al., 1995, *Proc. Natl. Acad. Sci. U.S.A.* 92:87-91) cleavage of heteroduplex DNA, methods based on oligonucleotide-specific primer extension (Syvanen et al., 1990, *Genomics* 8:684-692), genetic bit analysis (Nikiforov et al., 1994, *Nucl Acids Res* 22:4167-4175), oligonucleotide-ligation assay (Landegren et al., 1988, *Science* 241:1077), oligonucleotide-specific ligation chain reaction ("LCR") (Barrany, 1991, *Proc. Natl. Acad. Sci. U.S.A.* 88:189-193), gap-LCR (Abravaya et al., 1995, *Nucl. Acids Res* 23:675-682), radioactive or fluorescent DNA sequencing using standard procedures well known in the art, and peptide nucleic acid (PNA) assays (Orum et al., 1993, *Nucl. Acids Res.* 21:5332-5356; Thiede et al., 1996, *Nucl. Acids Res.* 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, *J. Mol. Biol.* 98:503-517), single stranded conformational polymorphism analyses (SSCP) (Orita et al., 1989, *Proc. Natl. Acad. Sci. USA* 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine the length of envelope protein variable regions and/or number of envelope protein glycosylation sites in the env gene.

These techniques can easily be adapted to provide high-throughput methods for determining the length of envelope protein variable regions and/or number of envelope protein glycosylation sites in viral genomes. For example, a gene array from Affymetrix (Affymetrix, Inc., Sunnyvale, Calif.) can be used to rapidly identify genotypes of a large number of individual viruses. Affymetrix gene arrays, and methods of making and using such arrays, are described in, for example, U.S. Pat. Nos. 6,551,784, 6,548,257, 6,505,125, 6,489,114, 6,451,536, 6,410,229, 6,391,550, 6,379,895, 6,355,432, 6,342,355, 6,333,155, 6,308,170, 6,291,183, 6,287,850, 6,261,776, 6,225,625, 6,197,506, 6,168,948, 6,156,501, 6,141,096, 6,040,138, 6,022,963, 5,919,523, 5,837,832, 5,744,305, 5,834,758, and 5,631,734, each of which is hereby incorporated by reference in its entirety.

In addition, Ausubel et al., eds., *Current Protocols in Molecular Biology,* 2002, Vol. 4, Unit 25B, Ch. 22, which is hereby incorporated by reference in its entirety, provides further guidance on construction and use of a gene array for determining the genotypes of a large number of viral isolates. Finally, U.S. Pat. Nos. 6,670,124; 6,617,112; 6,309,823; 6,284,465; and 5,723,320, each of which is incorporated by reference in its entirety, describe related array technologies that can readily be adapted for rapid identification of a large number of viral genotypes by one of skill in the art.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine the length of envelope protein variable regions and/or number of envelope protein glycosylation sites.

Additionally, the nucleic acid can be sequenced by any sequencing method known in the art. For example, the viral DNA can be sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499. See also the techniques described in Sambrook et al., 2001, *Molecular Cloning: A Laboratory Manual*, Cold Spring Harbor Laboratory, $3^{rd}$ ed., NY; and Ausubel et al., 1989, *Current Protocols in Molecular Biology*, Greene Publishing Associates and Wiley Interscience, NY.

Antibodies directed against the viral gene products, i.e., viral proteins or viral peptide fragments can also be used to detect amino acids associated with enhanced ability to enter a cell expressing CD4 and CXCR4 in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

6.3 Computer-Implemented Methods for Determining Whether an HIV or HIV Population has an Enhanced Ability to Enter Cells Expressing CD4 and CXCR4

In another aspect, the present invention provides computer-implemented methods for determining whether an HIV is likely to have an enhanced ability to enter a cell expressing CD4 and CXCR4. In such embodiments, the methods of the invention are adapted to take advantage of the processing power of modern computers. One of skill in the art can readily adapt the methods in such a manner. Therefore, in certain embodiments, the invention provides a computer-implemented method for determining whether an HIV is likely to have an enhanced ability to enter a cell expressing CD4 and CXCR4 relative to a reference HIV, comprising inputting genotypic information into a memory system of a computer, wherein the genotypic information indicates that the envelope protein of the HIV comprises a codon encoding valine in a codon corresponding to codon 515 of HIV strain HXB2, a codon encoding valine in a codon corresponding to codon 539 of HIV strain HXB2, or a codon encoding alanine in a codon corresponding to codon 607 of HIV strain HXB2; inputting a correlation between the presence of a codon encoding valine in a codon corresponding to codon 515 of HIV strain HXB2, a codon encoding valine in a codon corresponding to codon 539 of HIV strain HXB2, or a codon encoding alanine in a codon corresponding to codon 607 of HIV strain HXB2 and enhanced ability to enter a cell expressing CD4 and CXCR4 into the memory system of the computer, and determining whether the HIV is likely to have enhanced ability to enter a cell expressing CD4 and CXCR4 relative to a reference HIV.

In certain embodiments, the reference HIV is NL4-3, HXB2, or SF2. In certain embodiments, the reference HIV has an envelope gene that encodes an envelope protein having a sequence identical to the envelope protein of the HIV except for one or more differences at a codon corresponding to codon 515, 539, or 607 of HIV strain HXB2.

In certain embodiments, the genetic information indicates that the envelope protein comprises a valine at codon 515. In certain embodiments, the genetic information indicates that the envelope protein comprises a valine at codon 539. In certain embodiments, the genetic information indicates that the envelope protein comprises an alanine at codon 607. In certain embodiments, the genetic information indicates that the envelope protein comprises a valine at codon 515 and a valine at codon 539. In certain embodiments, the genetic information indicates that the envelope protein comprises a valine at codon 515 and an alanine at codon 607. In certain embodiments, the genetic information indicates that the envelope protein comprises a valine at codon 515, a valine at codon 539, and an alanine at codon 607.

In other embodiments, the invention provides a computer-implemented method for determining whether an is likely to have an enhanced ability to enter a cell expressing CD4 and CXCR4 relative to a reference HIV, comprising inputting genotypic information into a memory system of a computer, wherein the genotypic information comprises at least a portion of the sequence of the envelope protein of the HIV and a corresponding portion of the sequence of the envelope protein of the reference HIV, comparing the sequences of the envelope proteins of the HIV and the reference HIV, and determining whether the HIV is likely to have an enhanced ability to enter a cell expressing CD4 and CXCR4, wherein the presence of a valine at codon 515, a valine at codon 539, or an alanine at codon 607, wherein the positions of the codons correspond to HIV strain HXB2, in the HIV but not in the reference HIV indicates that the HIV is likely to have an enhanced ability to enter the cell expressing CD4 and CXCR4 relative to the reference HIV.

In certain embodiments, the methods further comprise displaying that the HIV is likely to have an enhanced ability to enter a cell expressing CD4 and CXCR4 relative to a reference HIV on a display of the computer. In certain embodiments, the methods further comprise printing the HIV is likely to have an enhanced ability to enter a cell expressing CD4 and CXCR4 than a reference HIV.

In another aspect, the invention provides a tangible medium indicating the HIV is likely to have an enhanced ability to enter a cell expressing CD4 and CXCR4 relative to a reference HIV produced according to a method of the invention. In certain embodiments, the tangible medium is a computer-readable medium. In certain embodiments, the tangible medium is a paper document. In certain embodiments, the paper document is a printed document, e.g., a computer printout. In still another aspect, the invention provides a computer-readable medium comprising data indicating the HIV is likely to have an enhanced ability to enter a cell expressing CD4 and CXCR4 relative to a reference HIV produced according to a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In still another aspect, the invention provides an article of manufacture that comprises computer-readable instructions for performing a method of the invention. In certain embodiments, the article of manufacture is a random-access memory. In certain embodiments, the article of manufacture is a fixed disk. In certain embodiments, the article of manufacture is a floppy disk. In certain embodiments, the article of manufacture is a portable memory device, such as, e.g., a USB key or an iPod™.

In yet another aspect, the invention provides a computer-readable medium that comprises data indicating the HIV is likely to have an enhanced ability to enter a cell expressing CD4 and CXCR4 than a reference HIV and computer-readable instructions for performing a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In yet another aspect, the invention provides a computer system that is configured to perform a method of the invention.

6.4 Viruses and Viral Samples

Envelope protein sequences, or nucleic acid sequences encoding envelope proteins, can be determined from a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, envelope protein sequences, or nucleic acid sequences encoding envelope proteins, can be determined from a virus that is obtained from a culture. In some embodiments, the culture can be obtained from a laboratory. In other embodiments, the culture can be obtained from a collection, for example, the American Type Culture Collection.

In certain embodiments, envelope protein sequences, or nucleic acid sequences encoding envelope proteins, can be determined from a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. application Ser. No. 09/874,475 and 10/077,027, each of which is incorporated herein by reference. In certain embodiments, the genes can be those that encode envelope protein (gp160).

In another embodiment, the intact virus need not be used. Instead, a part of the virus incorporated into a vector can be used. Preferably that part of the virus is used that is targeted by an anti-viral drug.

In another embodiment, envelope protein sequences, or nucleic acid sequences encoding envelope proteins, can be determined in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure.

In certain embodiments, the virus is HIV and the selective pressure is a NNRTI. In another embodiment, the virus is HIV-1 and the selective pressure is a NNRTI. Any NNRTI can be used to apply the selective pressure. Examples of NNRTIs include, but are not limited to, nevirapine, delavirdine and efavirenz. By treating HIV cultured in vitro with a NNRTI, one can select for mutant strains of HIV that have decreased susceptibility to the NNRTI. The stringency of the selective pressure can be manipulated to increase or decrease the survival of viruses not having the selected-for characteristic.

In other embodiments, the virus is HIV and the selective pressure is a NRTI. In another embodiment, the virus is HIV-1 and the selective pressure is a NRTI. Any NRTI can be used to apply the selective pressure. Examples of NRTIs include, but are not limited to, AZT, ddI, ddC, d4T, 3TC, abacavir, and tenofovir. By treating HIV cultured in vitro with a NRTI, one can select for mutant strains of HIV that have decreased susceptibility to the NRTI. The stringency of the selective pressure can be manipulated to increase or decrease the survival of viruses not having the selected-for characteristic.

In still other embodiments, the virus is HIV and the selective pressure is a PI. In another embodiment, the virus is HIV-1 and the selective pressure is a PI. Any PI can be used to apply the selective pressure. Examples of P is include, but are not limited to, saquinavir, ritonavir, indinavir, nelfinavir, amprenavir, lopinavir and atazanavir. By treating HIV cultured in vitro with a PI, one can select for mutant strains of HIV that have decreased susceptibility to the PI. The stringency of the selective pressure can be manipulated to increase or decrease the survival of viruses not having the selected-for characteristic.

In still other embodiments, the virus is HIV and the selective pressure is an entry inhibitor. In another embodiment, the virus is HIV-1 and the selective pressure is an entry inhibitor. Any entry inhibitor can be used to apply the selective pressure. An example of a entry inhibitor includes, but is not limited to, fusion inhibitors such as, for example, enfuvirtide. Other entry inhibitors include co-receptor inhibitors, such as, for example, AMD3100 (Anormed). Such co-receptor inhibitors can include any compound that interferes with an interaction between HIV and a co-receptor, e.g., CCR5 or CRCX4, without limitation. Still other entry inhibitors include UK-427857 (Pfizer), TNX-355 (Tanox Inc.), AMD-070 (AnorMED), Pro 140 (Progenics), FP-21399 (EMD Lexigen), BMS-488043 (Bristol-Myers Squibb), and GSK-873,140 (GlaxoSmithKline). By treating HIV cultured in vitro with an entry inhibitor, one can select for mutant strains of HIV that have decreased susceptibility to the entry inhibitor. The stringency of the selective pressure can be manipulated to increase or decrease the survival of viruses not having the selected-for characteristic.

In another aspect, envelope protein sequences, or nucleic acid sequences encoding envelope proteins, associated with enhanced ability to enter a cell expressing CD4 and CXCR4 according to the present invention can be made by mutagenizing a virus, a viral genome, or a part of a viral genome. Any method of mutagenesis known in the art can be used for this purpose. In certain embodiments, the mutagenesis is essentially random. In certain embodiments, the essentially random mutagenesis is performed by exposing the virus, viral genome or part of the viral genome to a mutagenic treatment. In another embodiment, a gene that encodes a viral protein that is the target of an anti-viral therapy is mutagenized.

Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, *Proc. Nat. Acad. Sci. USA* 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, envelope protein sequences, or nucleic acid sequences encoding envelope proteins, associated with enhanced ability to enter a cell expressing CD4 and CXCR4 can be identified in an HIV or HIV derivative made using site-directed mutagenesis. Any method of site-directed mutagenesis known in the art can be used (see e.g., Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY). See, e.g., Sarkar et al., 1990, *Biotechniques,* 8:404-407. The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV envelope protein. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains that are resistant or susceptible or hypersusceptible to one or more antiviral agents. In another embodiment, the mutagenized nucleotides encode amino acid residues that are adjacent to or near in the primary sequence of the protein residues known or suspected to interact with an anti-viral compound or known or suspected to be mutated in viral strains that are resistant or susceptible or hypersusceptible to one or more antiviral agents. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having an altered replication capacity. In another embodiment, the mutagenized nucleotides encode amino acid residues in or near the active site of a protein that is known or suspected to bind to an anti-viral compound.

7. EXAMPLES

The following examples are presented to further illustrate and explain the present invention and should not be taken as limiting in any regard. Certain of these experiments were also described in U.S. application Ser. Nos. 09/874,475 and 10/077,027, each of which is incorporated by reference in its entirety. Further guidance regarding phenotypic drug susceptibility and resistance tests may be found in U.S. Pat. No. 5,837,464 (International Publication Number WO 97/27319) which is hereby incorporated by reference.

7.1 Example 1

Measuring the Ability of HIV-1 to Enter Cells in the Presence and Absence of Entry Inhibitors This example provides a method for accurately and reproducibly measuring the ability of HIV-1 to enter cells in the presence and absence of entry inhibitors. The methods described in this example can be used, for example, to assess the ability of HIV-1 to enter cells expressing particular receptors (e.g., CD4) and co-receptors (e.g., CCR5 and CXCR4), e.g., viral tropism, and, for example, to determine resistance or susceptibility to inhibitors of HIV-1 attachment and entry (heretofore collectively referred to as entry). This example further provides a means and method for measuring alterations (increases and decreases) in susceptibility to entry inhibitors.

One vector, an example of the envelope expression vector, (pHIVenv) was designed to express the envelope polyprotein (gp160) encoded by subject derived HIV envelope sequences (FIG. 1). Gp160 is subsequently cleaved by a cellular protease to generate the surface (gp120SU) and transmembrane (gp41™) subunits that comprise the envelope protein on the surface of HIV-1 virus particles. A second vector, an example of the viral expression vector, (either pHIVluc or pHIVlucΔU3) was designed to express genomic and subgenomic viral RNAs and all HIV proteins except the envelope polyprotein (FIGS. 1A-1B).

In this example, patient-derived segment(s) correspond to the coding region (~2.5 KB) of the HIV-1 envelope polyprotein (gp160) and represent envelope sequences amplified by the reverse transcription-polymerase chain reaction method CRT-PCR) using viral RNA isolated from virus derived from HIV-infected individuals, or envelope sequences derived from molecular clones of HIV-1 that contain specific mutations introduced by site directed mutagenesis of a parental molecular clone (typically NL4-3), or recombinant envelope sequences constructed from different patient clones as described below.

Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase, e.g. Superscript II (Invitrogen, Life Technologies), Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into first strand cDNA. The cDNA was then amplified to high copy number using a thermostable DNA polymerase, e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216-2220), e.g. Expand High Fidelity PCR System (Taq+Pwo), (Boehringer Mannheim. Indianapolis, Ind.) or GeneAmp XL PCR kit (Tth+Vent), (Roche Molecular Systems, Inc., Branchburg, N.J.), Advantage-2, (CloneTech).

Oligo-dT was used for reverse transcription of viral RNA into first strand cDNA. Envelope PCR primers, forward primer Xho/Pin and reverse primer Mlu/Xba (Table 3) were used to amplify the patient-derived segments. These primers were designed to amplify the ~2.5 kB envelope gene encoding the gp160 envelope polyprotein, while introducing Xho I and Pin AI recognition sites at the 5' end of the PCR amplification product, and Mlu I and Xba I sites at the 3' end of the PCR amplification product.

Subject derived segments (2.5 kB envelope sequence amplification product) were inserted into HIV-1 envelope expression vectors using restriction endonuclease digestion, DNA ligation and bacterial transformation methods as described in U.S. application Ser. Nos. 09/874,475 and 10/077,027. The 2.5 kB amplification product was digested with either Xho I or Pin AI at the 5' end and either Mlu I or Xba I at the 3' end. The resulting digestion products were ligated, using DNA ligase, into the 5' Xho I/Pin AI and 3' Mlu I/Xba I sites of modified pCXAS or pCXAT expression vectors. The construction of the pCXAS and pCXAT vectors was described in U.S. Pat. No. 5,837,464. Modified pCXAS and pCXAT vectors contain a Pin AI restriction site in addition to the Xho I, MluT and Xba I restriction sites that exist in pCXAS and pCXAT. The Pin AI site was introduced between the Xho I and Mlu I sites by site directed mutagenesis, such that the four sites are located 5' to 3' in the following order; Xho I, Pin AI, Mlu I and Xba I. In a preferred embodiment, the ~2.5 kB amplification products were digested with Pin AI and Mlu I and ligated into the 5' Pin AI site and the 3' Mlu I site of the modified pCXAS expression vector. Ligation reaction products were used to transform E. coli. Following a 24-36 h incubation period at 30-37° C., the expression vector plasmid DNA was purified from the E. coli cultures. To ensure that expression vector preparations adequately represents the HIV quasi-species present in the serum of a given subject, many (>100) independent E. coli transformants were pooled and used for the preparations of pHIVenv plasmid DNA. Vectors that are assembled in this manner for the purposes of expressing subject virus derived envelope proteins are collectively referred to as pHIVenv (FIG. 1A).

The genomic HIV expression vectors pHIVluc and pHIVlucΔU3 were designed to transcribe HIV genomic RNA and subgenomic mRNAs and to express all HIV proteins except the envelope polyprotein (FIG. 1B). In these vectors, a portion of the envelope gene has been deleted to accommodate a functional indicator gene cassette, in this case, firefly luciferase, that is used to monitor the ability of the virus to replicate in the presence or absence of anti-viral drugs. In pHIVlucΔU3, a portion of the 3' U3 region has been deleted to prevent transcription of viral RNAs from the 5' LTR in infected cells.

Susceptibility assays for HIV-1 entry inhibitors were performed using packaging host cells consisting of the human embryonic kidney cell line 293 (Cell Culture Facility, UC San Francisco, SF, CA) and target host cells consisting of a human osteosarcoma (HOS) cell line expressing CD4 (HT4) plus CCR5, and CXCR4, astrocytoma (U-87) cell lines expressing either CD4 and CCR5 or CD4 and CXCR4, or glioma (NP2) cell lines expressing CD4 and either CCR5 or CXCR4. FIG. 6 shows that the relative results achieved from monitoring HIV-1 entry mediated by envelope proteins from three different individual patient clones were consistent in both U87 and NP2 cells expressing CD4 and CCR5 or CXCR4.

Drug susceptibility and tropism testing was performed using pHIVenv and pHIVluc or pHIVlucΔU3. Pseudotyped HIV particles containing envelope proteins encoded by the subject derived segment were produced by transfecting a packaging host cell (HEK 293) with resistance test vector DNA. Virus particles were collected (~48 h) after transfection and were used to infect target cells (HT4/CCR5/CXCR4, or U-87/CD4/CXCR4, or U-87/CD4/CCR5, or NP2/CD4/CXCR4 or NP2/CD4/CCR5) that express HIV receptors (i.e. CD4) and co-receptors (i.e. CXCR4, CCR5). After infection (~72 h) the target cells were lysed and luciferase activity was measured. HIV must complete one round of replication to successfully infect the target host cell and produce luciferase activity. The amount of luciferase activity detected in the infected cells was used as a direct measure of "infectivity" (FIGS. 1 and 2). If for any reason (e.g., lack of the appropriate receptor or co-receptor, inhibitory drug activity, neutralizing antibody binding) the virus was unable to enter the target cell luciferase activity is diminished. Drug susceptibility was assessed by comparing the infectivity in the absence of drug to infectivity in the presence of drug. Relative drug susceptibility can be quantified by comparing the susceptibility of the "test" virus to the susceptibility of a well-characterized reference virus (wild type) derived from a molecular clone of HIV-1, for example NL4-3 or HXB2.

The ability of a virus to enter a cell was assessed by comparing the amount of luciferase activity produced in each cell type, e.g., cells expressing CD4 and either CCR5 or CXCR4, both in the presence and absence of drug. The results of the assay were interpreted by comparing the ability of each virus to infect (produce luciferase activity) in cells expressing CCR5 or CXCR4, or both, if the virus is dual tropic. The ability of a CCR5 or CXCR4 inhibitor to specifically block infection (inhibit luciferase activity) was also evaluated (FIG. 3). X4 tropic viruses infect X4 cells but not R5 cells and infection of X4 cells is blocked by a CXCR4 inhibitor, e.g., AMD3100. Similarly, R5 tropic viruses infect R5 cells but not X4 cells and infection of R5 cells is blocked by a CCR5 inhibitor, e.g., a piperidin-lyl butane compound. Dual tropic, or mixtures of X4 and R5 tropic viruses, infect both X4 and R5 cells and infection of CCR5-expressing cells is blocked by the CCR5 inhibitor and infection of CXCR4-expressing cells is blocked by the CXCR4 inhibitor. Non-viable viruses do not replicate in either X4 or R5 cells (e.g., luciferase activity is not produced).

Packaging host cells were seeded in 10-cm-diameter dishes and were transfected one day after plating with pHIVenv and pHIVluc or pHIVlucΔU3. Transfections were performed using a calcium-phosphate co-precipitation procedure. The cell culture media containing the DNA precipitate was replaced with fresh medium, from one to 24 hours, after transfection. Cell culture media containing viral particles was typically harvested 2 days after transfection and was passed through a 0.45-mm filter. Before infection, target cells were plated in cell culture media. When used, entry inhibitor drugs were typically added to target cells at the time of infection (one day prior to infection on occasion). Typically, 3 days after infection target cells were assayed for luciferase activity using the Steady-Glo reagent (Promega) and a luminometer.

7.2 Example 2

Identifying Envelope Amino Acid Sequence Differences that Affect Susceptibility to Virus Entry Inhibitors or Viral Tropism This example provides a means and method for identifying mutations in HIV-1 envelope that affect susceptibility to virus entry inhibitors or virus tropism. This example also provides a means and method for quantifying the degree of altered susceptibility to entry inhibitors conferred by specific envelope mutations. This example further provides a means and method for quantifying the degree of effects on the ability of HIV-1 to enter CCR5- or CXCR4-expressing cells conferred by specific envelope sequences.

Envelope sequences derived from subject samples, or individual clones derived from subject samples, or envelope sequences engineered by site directed mutagenesis to contain specific mutations, were tested in the entry assay described above to quantify drug susceptibility and/or virus tropism based on a well-characterized reference standard (e.g. NL4-3, HXB2).

In one embodiment, susceptibility to longitudinal subject samples (viruses collected from the same subject at different timepoints) is evaluated. For example, susceptibility to entry inhibitors and/or virus tropism is measured prior to initiating therapy, before or after changes in drug treatment, or before or after changes in virologic (RNA copy number), immunologic (CD4 T-cells), or clinical (opportunistic infection) markers of disease progression.

7.2.1 Genotypic Analysis of Subject HIV Samples

Envelope sequences representing subject sample pools, or clones derived from subject pools, can be analyzed by any broadly available DNA sequencing methods. In this example, subject HIV sample sequences were determined using viral RNA purification, RT/PCR and dideoxynucleotide chain terminator sequencing chemistry and capillary gel electrophoresis (Applied Biosystems, Foster City, Calif.). Envelope sequences of subject virus pools or clones were compared to reference sequences and other subject samples. The genotypes of the viruses were examined for sequences that are different from the reference or pre-treatment sequence and correlated to differences in entry inhibitor susceptibility, as described below.

7.2.2 Entry Inhibitor Susceptibility of Site Directed Mutants

Genotypic changes that correlate with changes in susceptibility to entry inhibitors, and/or viral tropism can be evaluated by constructing envelope expression vectors (pHIVenv) containing the specific mutation on a defined, drug susceptible, genetic background (e.g. NL4-3 reference strain). Mutations may be incorporated alone and/or in combination with other mutations that are thought to modulate the entry inhibitor susceptibility. Envelope mutations are introduced into pHIVenv vectors using any of the broadly available methods for site-directed mutagenesis. In certain embodiments the mega-primer PCR method for site-directed mutagenesis is used (Sarkar et al., 1990, *Biotechniques* 8(4):404-07). A pHIVenv vector containing a specific envelope mutation or group of mutations are tested using the virus entry assay described in Example 1. Drug susceptibility and/or tropism of the virus containing envelope mutations is compared to the drug susceptibility and/or tropism of a genetically defined drug susceptible virus that lacks the specific mutations under evaluation. Observed changes in entry inhibitor susceptibility and/or tropism are attributed to the specific mutations introduced into the pHIVenv vector.

7.3 Example 3

Measuring Susceptibility to Virus Entry Inhibitors to Guide Treatment Decisions

This example provides a means and method for using virus entry inhibitor susceptibility to guide the treatment of HIV-1. This example further provides a means and method for using virus entry inhibitor susceptibility to guide the treatment of subjects that have received previous antiretroviral treatment with a virus entry inhibitor. This invention further provides the means and methods for using virus entry inhibitor suscep-tibility to guide the treatment of subjects that have not received previous treatment with a virus entry inhibitor.

In one embodiment, the susceptibility of subject's viruses to virus entry inhibitors is used to guide the treatment of subjects failing antiretroviral regimens that include one or more virus entry inhibitors. Treatment failure (also referred to as virologic failure) is generally defined as partially suppressive antiviral treatment resulting in detectable levels of virus, which is typically measured in the subject plasma. Guidance may include, but is not limited to, (a) clarification of available drug treatment options, (b) selection of more active treatment regimens, (c) clarification of the etiology of rising viral load in treated subjects (i.e. poor adherence, drug resistance), and (d) reduction in the use of inactive and potentially toxic drugs. In this embodiment, resistance test vectors are derived from subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonists (e.g., AMD3100, AMD8664, TAK779, PR0542, and peperidin-lyl butane compounds) and CD4 antagonists (e.g., MAb B4). Appropriate treatment decisions are based on the results of the virus entry assay (e.g. see FIG. 4B) and additional relevant laboratory test results and clinical information.

In another embodiment, the susceptibility of subject's viruses to virus entry inhibitors is used to guide the treatment of subjects that have not been previously treated with antiretroviral regimens that include one or more virus entry inhibitors. Guidance may include, but is not limited to, (a) clarification of available drug treatment options, (b) selection of more active treatment regimens, (c) clarification of the baseline susceptibility to virus entry inhibitors, and (d) reduction in the use of inactive and potentially toxic drugs. Determining baseline susceptibility of virus entry inhibitors in treatment naive subjects is important for two reasons. First, the natural susceptibility of viruses to entry inhibitors can vary widely (e.g. see FIG. 4A). Second, the increased use of virus entry inhibitors will undoubtedly result in the generation of drug resistant variants that can be transmitted to newly infected individuals. In this embodiment, resistance test vectors are derived from subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonist (e.g. AMD3100, AMD8664, TAK-355, PR0542, and peperidin-lyl butane compounds) and CD4 antagonists (e.g. MAb 5A8). Appropriate treatment decisions are based on the results of the virus entry assay and additional relevant laboratory test results and clinical information.

7.4 Example 4

Assays Assessing Fusogenicity of HIV Envelope Proteins

This example provides means and methods for determining the fusogenicity, e.g., the propensity of a virus to mediate aggregation of susceptible cells and fusion of their membranes to form syncytia, of a virus's envelope protein. Briefly, nucleic acids encoding HIV-1 envelope proteins were amplified from patient plasma and introduced to an expression vector as described above in Example 1. See FIG. 5. Membrane fusion was measured by co-culturing HEK-293 cells transiently transfected with an HIV genomic vector comprising a deletion of the env gene (similar to pHIVluc, described above, but lacking luciferase activity) and the expression vector and CD4/CCR5/CXCR4-positive 5.25 cells transformed with plasmids expressing both green fluorescent protein (GFP) and luciferase under control of the HIV-1 long terminal repeat (LTR). Fusion was visualized by detecting GFP activity and quantified by determining amounts of luciferase activity.

More specifically, the fusion assay was developed by replacing the U87 target cell line used in the entry assay with the 5.25.Luc4.M7 cell line. The 5.25.Luc4.M7 cell line was derived from the CEMX174 cell line and contains green fluorescent protein (GFP) and firefly luciferase (LUC) reporter genes. GFP and LUC expression in 5.25.Luc4.M7 cells is regulated by tat-induction of the HIV-1 LTR. The fusion assay was performed by co-transfecting 293 effector cells with an envelope deleted HIV genomic vector plus an HIV envelope expression vector. At 48 hours post-transfection, the 293 effector cells were harvested, washed thoroughly to remove virus particles, and added to 5.25.Luc4.M7 target cell cultures in the presence of a reverse transcriptase inhibitor to inhibit virus replication. Membrane fusion was triggered in the co-cultures by the interaction of the HIV envelope protein produced in the 293 effector cells with the CD4, CCR5 and/or CXCR4 expressed on the surface of the 5.25.Luc4.M7 target cells. The tat protein derived from the effector cells trans-activates the GFP and LUC reporter genes. In this assay, cell-cell fusion can be observed directly using fluorescence microscopy to view GFP expression, and can be accurately quantified using luciferase (or immunochemical detection of GFP).

7.5 Example 5

Identification and Characterization of Envelope Protein Sequence Determinants that Affect Co-Receptor Usage This example describes identification and characterization of molecular determinants in the envelope protein of HIV-1 that affect the ability of the HIV-1 to enter cells expressing a particular co-receptor, e.g., CCR5 or CXCR4. In the experiments described below, binding and entry of cells expressing CD4 and either CCR5 or CXCR4 in the presence and absence of entry inhibitors was assessed as described in Example 1. To determine genotypes of the envelope proteins for which entry and fusogenicity phenotypes were determined, envelope gene sequences were determined using viral RNA purification, RT/PCR and ABI chain terminator automated sequencing according to conventional protocols as described in Example 2.

First, the ability of 24 individual envelope clones isolated from a single patient sample to enter U87 cells expressing CD4 and either CCR5 or CXCR4 was determined according to the procedures described in Example 1. The results of these assays are shown in FIG. 7. While V3 loop sequences have long been recognized to affect the ability of HIV-1 to enter cells expressing different co-receptors, several of the clones had identical or nearly identical V3 sequences but different abilities to enter cells expressing CCR5 or CXCR4 co-receptors. For example, clones 6 and 14 had identical V3 sequences, but clone 6 could not enter cells expressing CD4 and CXCR4, while clone 14 was able to enter such cells. These results suggest that envelope sequences outside the V3 region can affect the ability of HIV-1 to enter cells expressing different co-receptors.

To begin to identify the molecular basis for the observed differences in ability to enter cells expressing CCR5 or CXCR4, chimeric envelope genes were constructed that comprise envelope sequences from clone 6, a CCR5-tropic clone and from either clone 13 or 14, which are both dual tropic (e.g., can enter cells expressing either CCR5 or CXCR4) clones. The ability of viral particles comprising envelope proteins expressed from the chimeric envelope genes to enter U87 cells expressing CD4 and either CCR5 or CXCR4 was tested as described in Example 1. The results of these experiments are provided in FIG. 8. As shown in FIG. 8, the chimeric envelope gene encoding gp120 from clone 6 and gp41 from clone 13 or 14 was able to enter both CXCR4 and CCR5-expressing cells, while the chimeric envelope gene encoding gp120 from clone 13 or 14 and gp41 from clone 6 was able to enter CCR5-expressing cells, but not CXCR4-expressing cells. Thus, the ability of the clones 13 and 14 clones to enter CXCR4-expressing cells mapped to the portion of the envelope gene encoding gp41.

To confirm this result, two additional chimeric envelope genes were constructed. In these constructs, the gp41-coding portion of the env gene from strain JRCSF was replaced with the gp41-coding region from either clone 13 or 14. JRCSF is a well-characterized CCR5-tropic lab strain, while, as discussed above, clones 13 and 14 are dual-tropic. The results of these experiments are provided in FIG. 9. As expected, viral particles comprising the chimeric envelope proteins were able to enter cells expressing CD4 and CRCX4, confirming that the gp41 protein of clones 13 and 14 conferred the ability to use the CXCR4 co-receptor.

To more finely map the molecular basis of this ability, eight additional chimeric envelope genes were constructed to more finely map the molecular basis of the 14 or 13 clone's ability to enter CXCR4-expressing cells. The four clones were constructed using conventional techniques to encode different portions of the gp41 protein from clone 14 or 13 in an otherwise clone 6 background. The particular portion of the gp41 protein from clone 14 or 13 used in the four additional clones is shown in FIG. 10. Also shown in FIG. 10 are the relative abilities of the four new clones, the clone 6/clone 14 and clone 6/clone 13 chimeras discussed above, and clones 6 and 14 to enter cells expressing CD4 and CCR5 or CXCR4.

As shown in FIG. 10, clone E, comprising amino acids corresponding to gp160 positions 508-624 of reference strain HXB2 (Accession No. AAB50262) from 14 in a 6 background, was able to enter cells expressing CXCR4, while clone H, comprising amino acids corresponding to gp160 positions 625-856 (the c-terminus) of reference strain HXB2 from clone 14, was not. Thus, the molecular determinant of the envelope protein from clone 14 that allowed entry into CXCR4-expressing cells was mapped to the gp41 region of clone 14 corresponding to amino acids 508-624 of reference strain HXB2 gp160. In contrast, none of the chimeras made that comprised less than the entire gp41 protein from clone 13 could unambiguously enter CXCR4-expressing cells. Clone E, comprising amino acids corresponding to gp160 positions 508-624 of reference strain HXB2 from clone 13 in a clone 6 background had an indeterminate phenotype whose ability to enter CXCR4-expressing cells could not be unambiguously determined.

Next, a series of chimeric envelope genes was constructed to assess the relative contributions of V3 loop and gp41 sequences to the ability to enter cells expressing CD4 and CXCR4 or CCR5. In brief, the portion of the envelope gene encoding the V3 loop from clone 24 or 22 was introduced into a clone 6, 13, or 14 background, and the ability of viral particles comprising chimeric envelope proteins expressed from the chimeric genes to enter into cells expressing CD4 and CCR5 or CXCR4 determined according to Example 1. Clones 6, 24, and 22 have V3 loop sequences associated with CCR5-tropism, CXCR4-tropism, and dual-tropism, respectively. The particular V3 loop sequences and results of these experiments are presented in FIG. 11.

As shown in FIG. 11, introduction of the V3 loop from clone 22 into a clone 6 background greatly decreased without completely eliminating the ability of the chimera to enter CCR5-expressing cells, but conferred the ability to enter CXCR4 expressing cells. In contrast, introducing the V3 loop from clone 24 into a clone 6 background essentially eliminated the ability to enter CCR5-expressing cells and conferred the ability to enter CXCR4-expressing cells. These results tend to confirm that the ability of clone 6 to enter CCR5-expressing cells depends on the V3 loop sequences of this clone rather than sequences external to the V3 loop, such as, e.g., gp41.

Further, FIG. 11 also shows that introduction of the V3 loop from clone 22 into a clone 13 background decreased without eliminating the ability of the chimera to enter CCR5-expressing cells and greatly increased the ability of the chimera to enter CXCR4 expressing cells. Introducing the V3 loop from clone 24 into a clone 13 background greatly decreased without completely eliminating the ability of the chimera to enter CCR5-expressing cells and greatly increased the ability to enter CXCR4 expressing cells. These results tend to show that the ability of clone 13 to enter CCR5-expressing cells is largely, but not entirely, dependent on V3 sequences. These results also show that the ability of clone 13 to enter CXCR4-expressing cells can be greatly increased by substituting the V3 region of clone 13 with a V3 region associated with this ability. Thus, both the V3 region and gp41 sequences appear to affect the ability to enter CXCR4-expressing cells, and the degree of the effect can be greatly increased by the presence of both sequences. Also, the ability of clone 13 to enter CCR5-expressing cells is greatly influenced by the V3 loop, suggesting that the non-V3 sequences from clone 13 only weakly affect the ability to enter such cells.

Finally, FIG. 11 also shows that introduction of the V3 loop from clone 22 into a clone 14 background decreased without eliminating the ability of the chimera to enter CCR5-expressing cells and increased the ability of the chimera to enter CXCR4 expressing cells. Introducing the V3 loop from clone 24 into a clone 13 background further decreased, but did not completely eliminate, the ability of the chimera to enter CCR5-expressing cells and further increased the ability to enter CXCR4 expressing cells. Thus, even in combination with a V3 region that does not confer any ability to enter CCR5-expressing cells, the non-V3 sequences from clone 14 were still able to mediate entry into CCR5-expressing cells. In addition, combining V3 loops from clone 24 or 22 with non-V3 sequences from clone 14 increased the ability to enter into CXCR4-expressing cells, confirming that both V3 sequences and non-V3 sequences affect usage of this co-receptor.

Collectively, these results demonstrated that non-V3 sequences can affect entry into both cells expressing CCR5 and cells expressing CXCR4. Further, these results permit identification of particular non-V3 sequences that increase the ability to enter cells expressing CXCR4. To identify these sequences, the gp160 sequences of clones 6, 13, and 14 were aligned as shown in FIG. 12. As indicated above, the ability of the envelope protein to mediate entry into CXCR4-expressing cells from clone 14 mapped to the region corresponding to amino acids 508-624 of reference strain HXB2. Comparison of sequences from this region between clones 6 and 14 revealed three sequence differences: G515V, A539V, and D607A. Accordingly, these positions were identified as increasing the ability of an HIV-1 to enter cells expressing the CXCR4 co-receptor.

Interestingly, clone 13, which had an indeterminate phenotype as discussed above, comprises only one of these three substitutions, A539V. Thus, each of positions 515, 539 and 607 appears to affect the ability of HIV-1 to enter via the CXCR4 co-receptor.

Finally, the effects of these sequence variations on resistance or susceptibility to CCR5 and CXCR4 inhibitors were analyzed. In brief, the ability of clones 6, 24, and 14, and several chimeras to enter cells expressing CD4 and either CCR5 or CXCR4 was tested in the presence of varying concentrations of CCR5 inhibitor L-832657 or CXCR4 inhibitor AMD3100. The results of these experiments are presented in FIG. 13.

Figure 13:
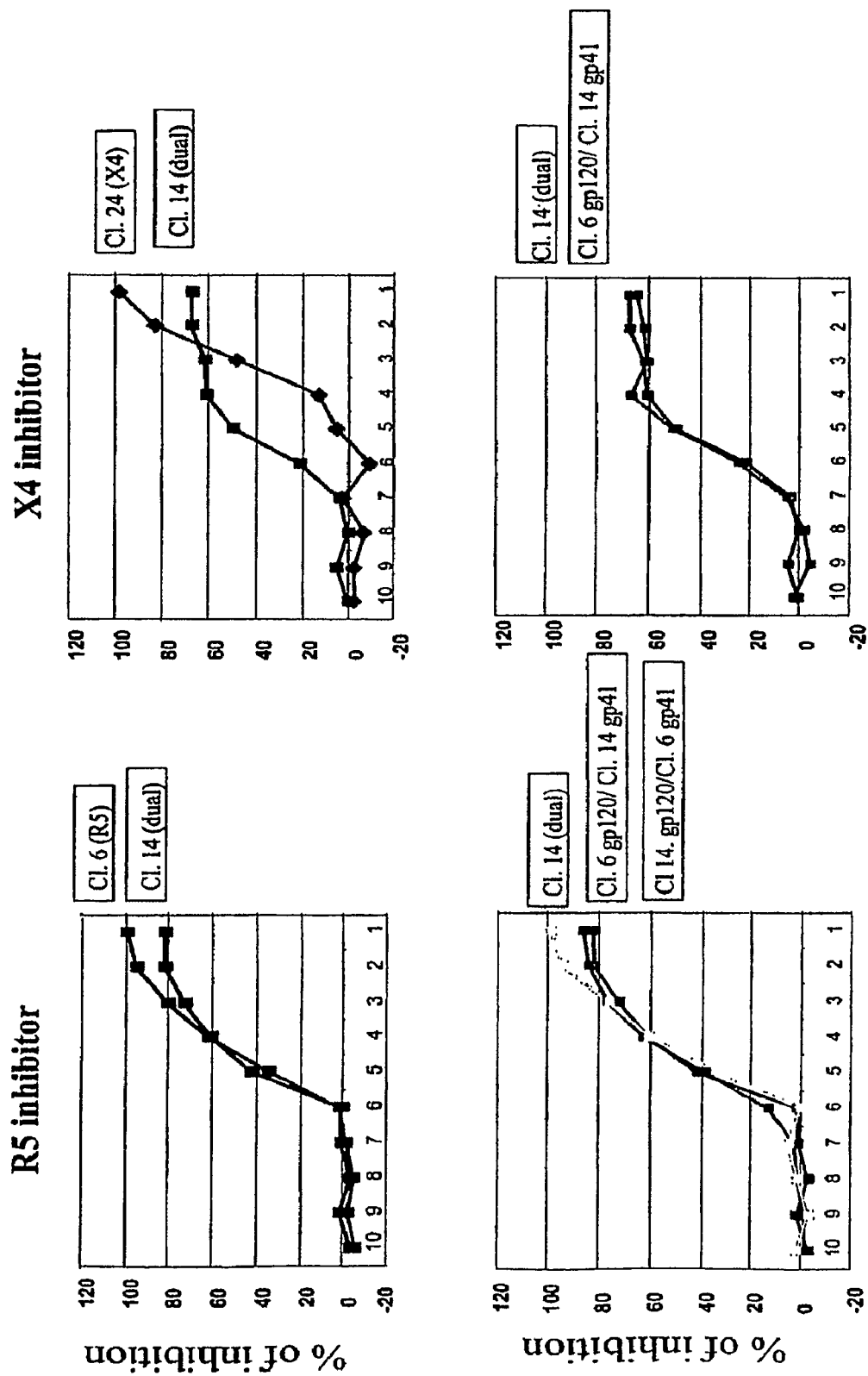

FIG. 13 shows that entry of viral particles having the envelope protein from clone 14 into either CXCR4- or CCR5-expressing cells cannot be completely inhibited, indicating that clone 14 has reduced susceptibility to both CCR5 and CXCR4 inhibitors. Accordingly, the susceptibility of the chimeras having gp120 from clone 6 and gp41 from clone 14 and gp120 from clone 14 and gp41 from clone 6 to such co-receptor inhibitors was tested to assess whether this reduced susceptibility maps to gp120 or gp41 of clone 14. As shown in FIG. 13, the chimera with gp120 from clone 14 and gp41 from clone 6 did not exhibit reduced susceptibility to L-832657, while the chimera with gp120 from clone 6 and gp41 from clone 14 exhibited reduced susceptibly to both a CCR5 and CXCR4 inhibitor similar to that observed for clone 14. Thus, clone 14's reduced susceptibility to the CCR5 and CXCR4 inhibitors mapped to the gp41 portion of clone 14.

7.6 Example 6

Confirmation of Envelope Protein Sequence Determinants that can Affect Co-Receptor Usage This example confirms that molecular determinants in the envelope protein of HIV-1, particularly in gp41 subunit, identified in Example 5 can affect the ability of the HIV-1 to enter cells expressing a particular co-receptor, e.g., CCR5 or CXCR4. In the experiments described below, binding and entry of cells expressing CD4 and either CCR5 or CXCR4 in the presence and absence of entry inhibitors was assessed as described in Example 1. To determine genotypes of the envelope proteins for which entry and fusogenicity phenotypes were determined, envelope gene sequences were determined using viral RNA purification, RT/PCR and ABI chain terminator automated sequencing according to conventional protocols as described in Example 2.

The ability of 22 individual envelope clones isolated from a single patient sample to enter U87 cells expressing CD4 and either CCR5 or CXCR4 was determined according to the procedures described in Example 1. Tropism results, luciferase results (relative light unit, RLU) and amino acid sequences of the V3 region are shown in Table 4.

Among these clones, eight clones were R5 tropic, one was X4-tropic and the remaining thirteen clones were dual-tropic. All R5-tropic clones had the same V3 amino acid sequence, while the clone that used CXCR4 exclusively contained nine different substitutions in V3: N7S, S11G, T13L, M14V, G17T, A19R, G24K, E25N and a deletion at position 16. Two different types of dual tropic clones were identified, designated dual-R and dual-X based on their ability to infect CXCR4 and CCR5 target cells and on their V3 sequences. Eight dual-X clones had similar V3 sequences that resembled that of the X4 tropic clone, with six different substitutions in V3: T13H, G17H, A19R, G24K and E25N, plus a deletion at position 16 compared to R5 clones. The dual clone 11 D contained one additional substitution R to G at position 3. In contrast, five dual-R tropic clones with V3 loop sequences identical to R5-tropic clones were identified.

The dual-R tropic clones showed lower infection on CXCR4 expressing cells (500 to $10^4$ RLU) compared to dual-X and X4 tropic clones ($10^4$ to $10^5$ RLU). Conversely, dual-R tropic clones displayed higher infection on CCR5 expressing cells ($10^5$ to $10^6$ RLU) than dual-tropic clones ($10^3$ to $10^4$ RLU), but comparable to R5 tropic clones ($10^5$ to $10^6$ RLU). All 22 clones were predicted to be R5-tropic based on the genotypic algorithms 11/25 rule (see Brumnuer et al., 2004, *AIDS* 18:F1-9) and position-specific scoring matrices (PSSM) (see Jensen et al., 2003, *J. Virology* 77:13376-13388) regardless of differences in phenotypic results. Taken together, these data suggest that sequences outside of the V3 loop of dual-R tropic clones may be responsible for CXCR4 co-receptor usage.

Figure 14:
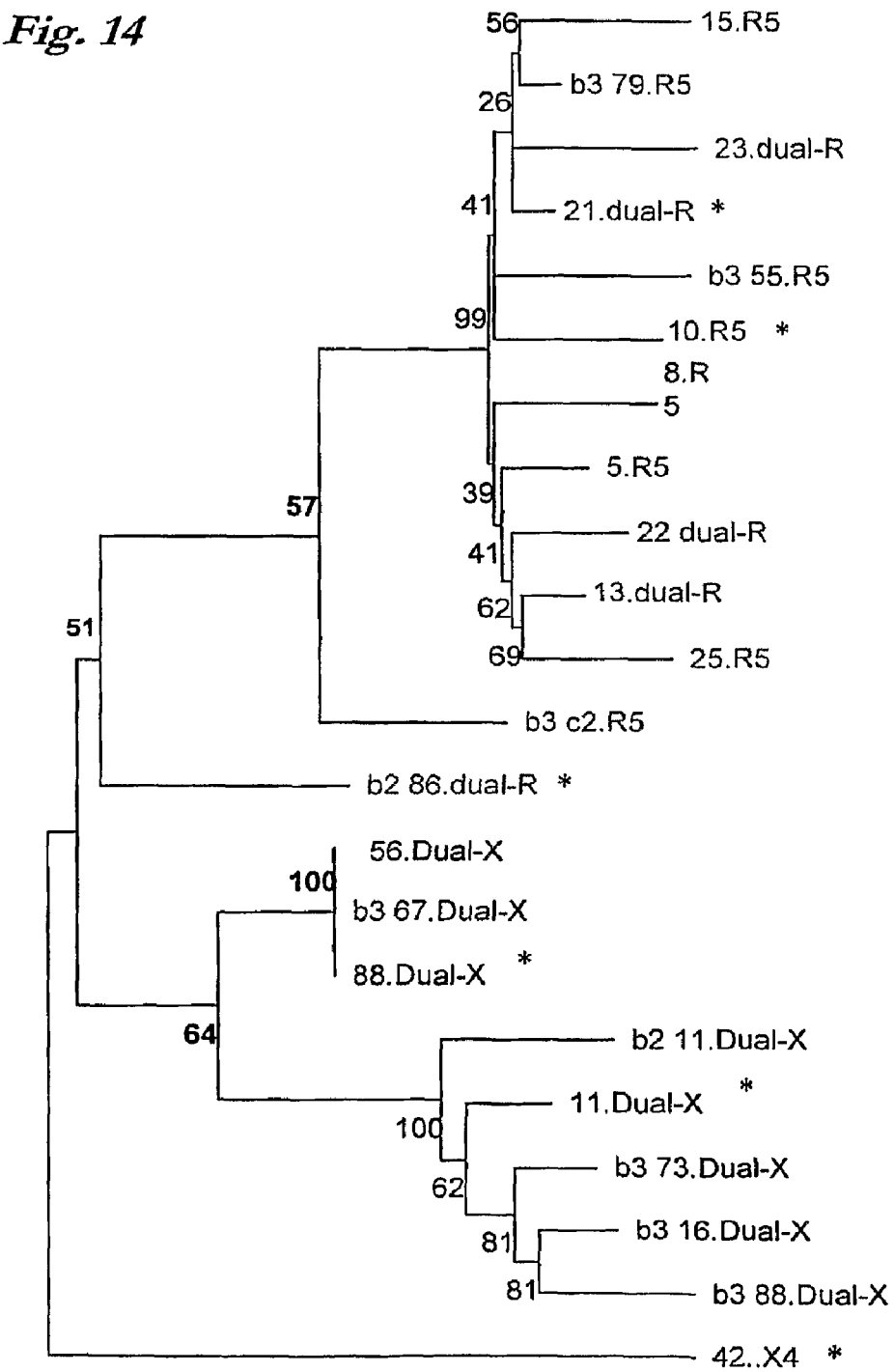

Phylogenetic analysis of gp160 env sequences of these env clones was performed using neighbor-joining methods in the software MEGA. See Kumar et al., 2004, *Brief Bioinform* 5(2):150-163. The results were shown in FIG. 14. The sequences of dual-R clones clustered with R5-tropic clones and were genetically distinct from dual-X tropic and X4-tropic clones in the neighbor-joining tree. Within 5 dual-R tropic clones, 86d, which had highest infection RLU on CXCR4 expressing cells, was also relatively more distant from other dual-R and R5 tropic clones, and relatively closer to dual-X and X4-tropic clones in the neighbor-joining tree.

Six env clones were selected for further investigation based on their differences in co-receptor tropism, V3 sequences and phylogenetic results: the R5-tropic clone 10r, the X4-tropic clone 42x, dual-X tropic clones 11D and 88D, and dual-R tropic clones 21d and 86d. The differences of translated amino acid sequences of gp120 (non-V3 region) and gp41 regions among these env clones are shown in Table 5. Compared to R5 tropic clone 10r, 11 to 30 amino acid changes were found in the env outside of V3 in other CXCR4-using clones. Dual-R clone 21d with lower luciferase activity on CXCR4 expressing cells contained the least number of substitutions (11 substitutions), dual-R clone 86d, with higher luciferase activity on CXCR4 expressing cells, had higher or similar numbers of substitutions (24 substitutions) compared to other dual-X clones (18-21 substitutions). Finally, the X4-tropic clone 42d showed most numbers of substitutions (30 substitutions).

Figure 15:
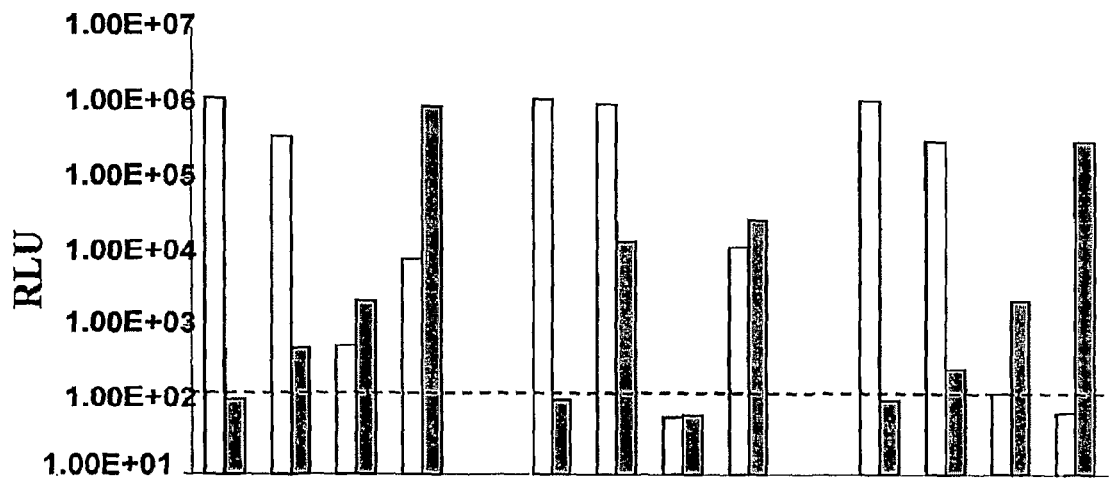

To evaluate the contribution of V3 and the rest of env to CXCR4 tropism, a panel of chimeras were constructed by exchanging the V3 regions between the R5-tropic clone 10r and 3 other CXCR4-using clones which had different V3 sequences: 11D, 88D and 42x. The co-receptor tropism of these chimeras and the amino acid sequence of their V3 loop are shown in FIG. 15. Three chimeras (numbers 2, 6 and 10) that contained the V3 region from clone 10r and the rest of env from either dual-X clones or X4-tropic clone retained some level of CXCR4 mediated entry activity. These results confirmed that some CXCR4 determinants were present outside of V3 loop sequence of the parental CXCR4-using clones 11D, 88D and 42x. Based on luciferase activity, virus infection of these chimeras with the R5 tropic like V3 was greatly increased on CCR5-expressing cells, but decreased on CXCR4-expressing cells compared to parental CXCR4-using clones (FIG. 15).

Three chimeras (number 3, 7 and 11) contained the V3 sequence from either dual-tropic (11D and 88D) or X4-tropic (42x) clones and the rest of env from R5-tropic clone 10r. Two of the chimeras (numbers 3 and 11) retained the CXCR4-using phenotypes as their parental clone 88D and 42x, but the level of infection was much lower. Chimera 7, which contained the V3 loop of the dual-tropic clone 11D, was not functional. A single amino acid substitution R3G in V3 loop completely diminished env mediated entry compared to chimeric env3 in the same backbone. The virus entry of chimeras containing R5-tropic env backbone with X4 like V3 loop was found to be much lower compared to their CXCR4-using parental clones (FIG. 15).

Figure 16:
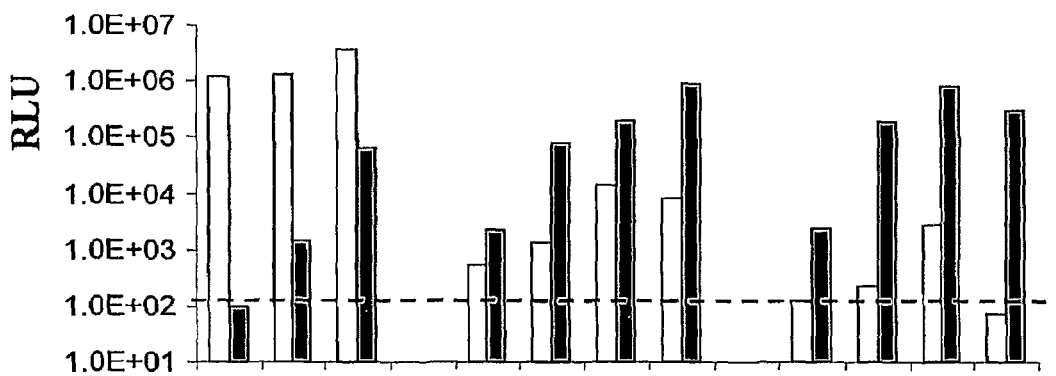

All chimeras with the dual-R tropic env backbone from 21d (numbers 5 and 9) and 86d (numbers 6 and 10) improved entry efficiency on both CXCR4 and CCR5 expressing cells better than the paired chimeras (numbers 4 and 8) bearing the R5 tropic backbone 10r (FIG. 16). The chimeras made from 86d (numbers 6 and 10) generated higher luciferase activity than that from 21d (numbers 5 and 9), which is consistent with higher luciferase activity observed in parental clone 86d than 21d. In comparison to the parental clones 10r, 21d and 86d, all chimeras with the V3 sequence from dual- or X4-tropic clones gained more luciferase activity in CXCR4-expressing cells but dramatically reduced their ability to infect CCR5-expressing cells (FIG. 16).

Taken together, these data provide additional indication that env regions outside of V3 contribute to efficient use of CXCR4.

Figure 17A:
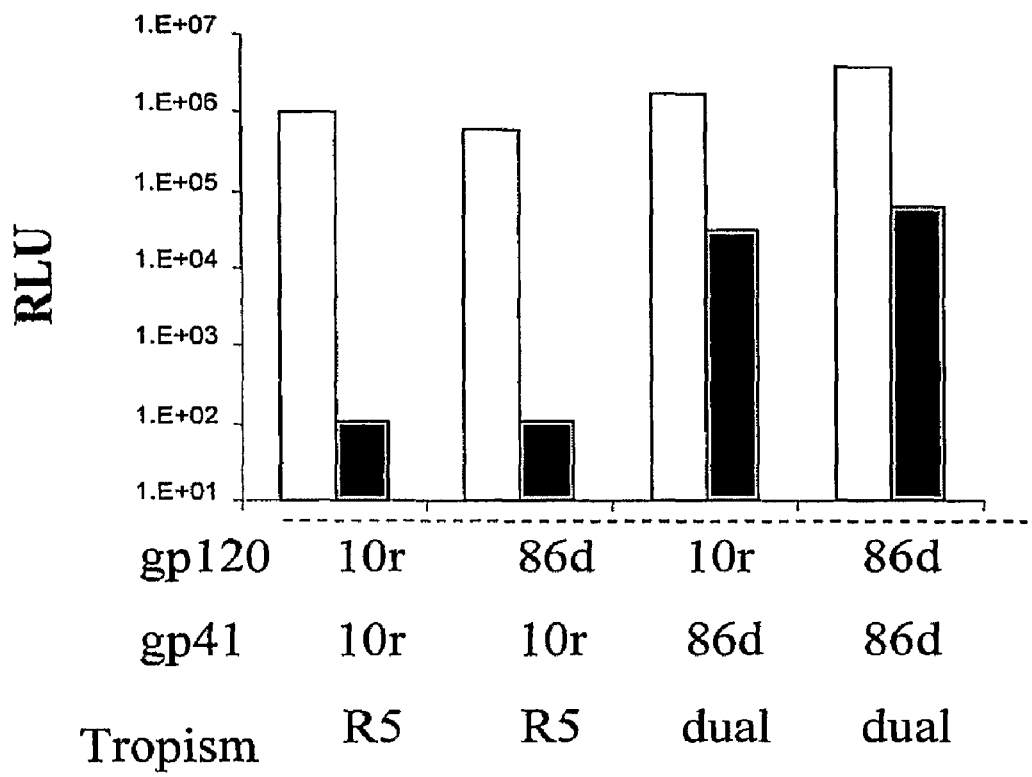
Figure 17B:
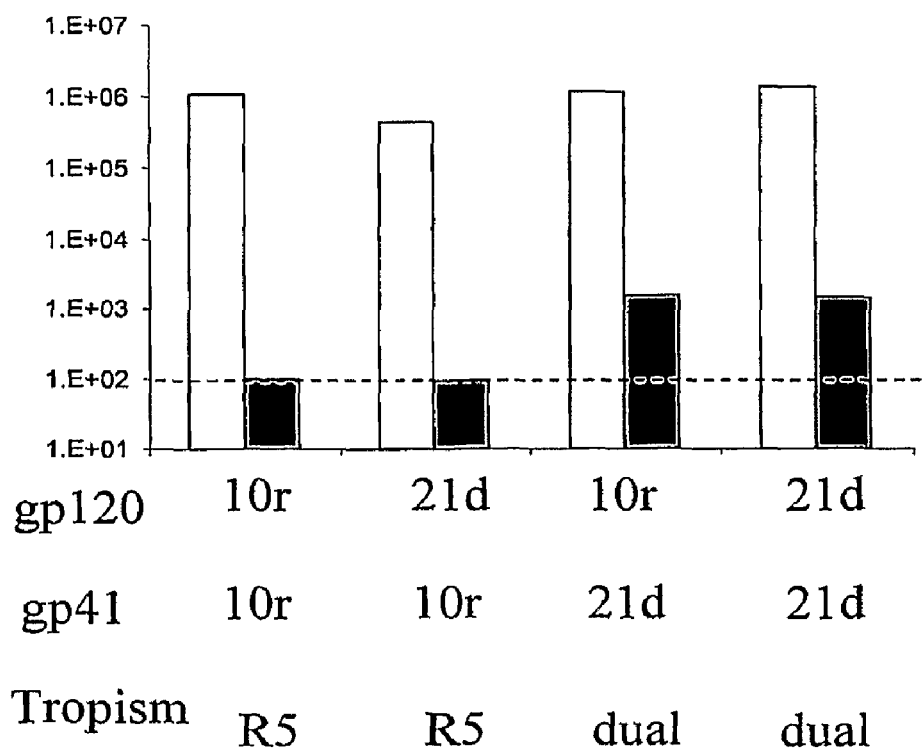
Figure 17C:
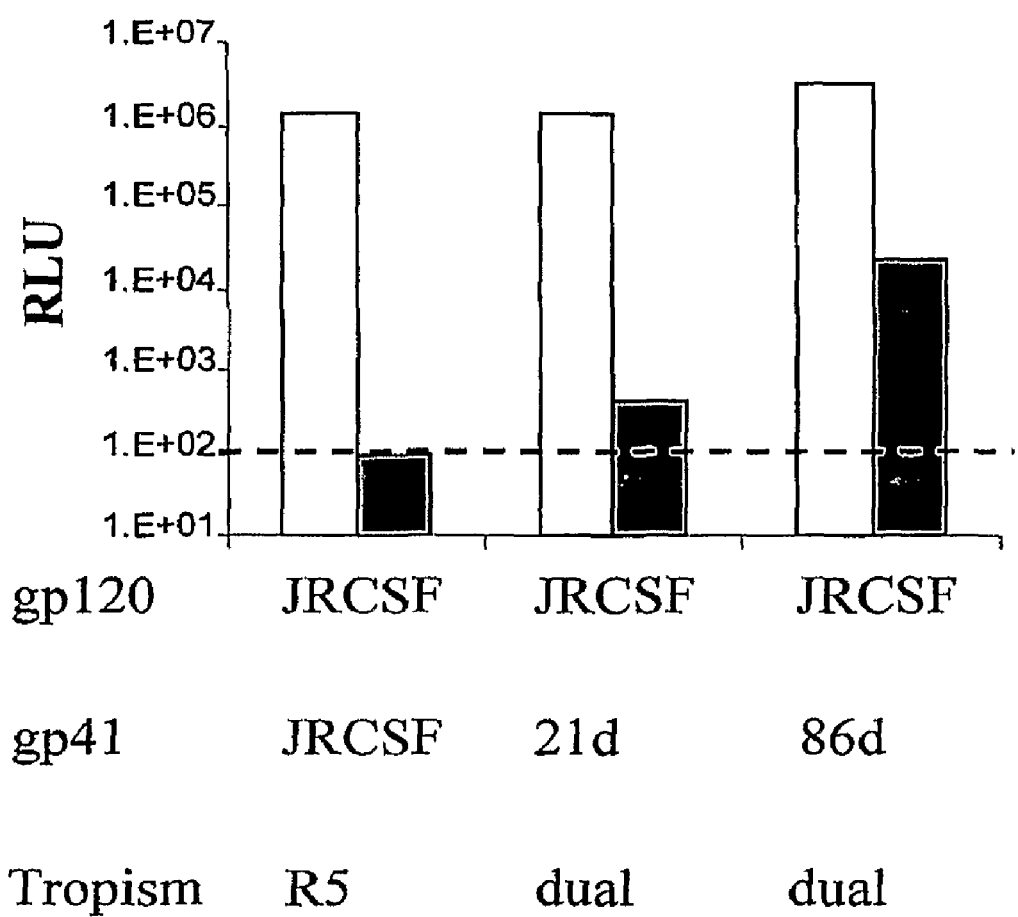

To identify CXCR4 determinants of dual-R tropic clones which exhibit R5-like V3 sequences, R5 clone 10r and two dual-R clone 21d and 86d were further analyzed. There were 11 and 24 amino acid differences in clone 21d and 86d compared to R5 clone 10r, respectively (Table 5). In clone 21d, 6 substitutions were present in gp120 and 5 substitutions were present in gp41. In clone 86d, there were 12 amino acid substitutions in gp120 and 12 in gp41. To localize domains required for the CXCR4-using phenotype, chimeric envs were constructed by exchanging the sequences of the gp120 and gp41 subunits between the dual-R and R5-tropic clones. Phenotype testing indicated that chimeras containing the gp120 sequence from the R5-tropic clone 10r and the gp41 sequence from the dual-R tropic clones 21d or 86d exhibited a dual-tropic phenotype, whereas chimeras that contained the gp120 sequence from the dual-tropic clone 21d or 86d and the gp41 sequence from the R5-tropic clone 10r showed an R5-tropic phenotype (FIGS. 17A and 17B). These results indicate that, in the dual-R tropic clones 21d and 86d, the determinants responsible for conferring CXCR4 use are located in gp41, not the gp120 sequence. To further confirm this observation, chimeric envs were constructed that contained the gp41 sequence from either clone 21d or 86d and the gp120 sequence from the unrelated R5-tropic strain JRCSF. In these experiments, both chimeric envs with the gp41 sequence from either 21d or 86d dual-R clones, were able to infect both CCR5 and CXCR4 target cells and thus retained the dual-tropic phenotype (FIG. 17C). These data confirmed that the determinants of CXCR4 use of dual-R clone 21d and 86d are located in gp41.

Figure 18A:
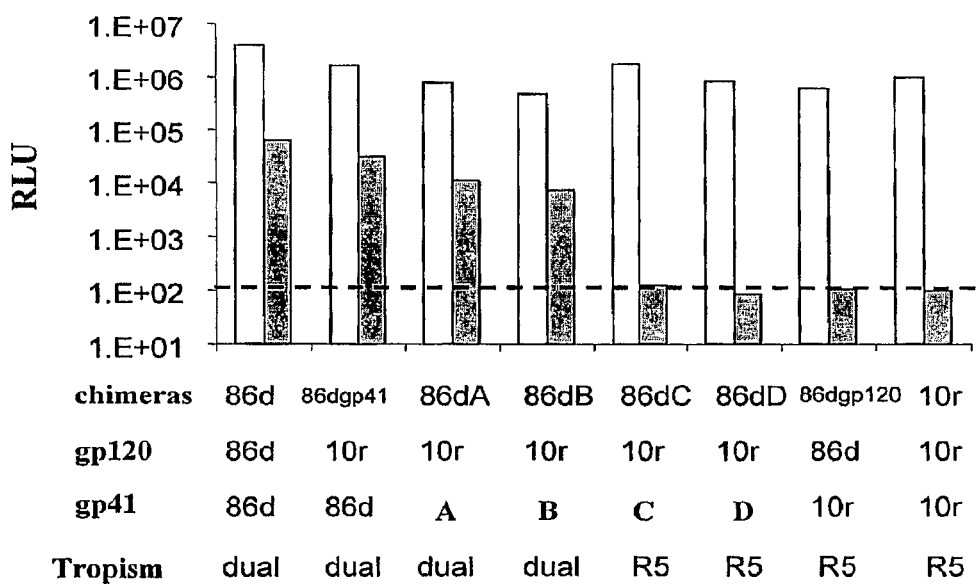

To define which substitutions within the gp41 subunit of dual-R tropic clones were responsible for CXCR4 use, R5-tropic clone 10r and dual-R tropic clone 86d were used for generation of additional chimeric env constructs. Four chimeras were made, each containing different sets of substitutions in gp41 of clone 86d on the env backbone clone 10r (FIG. 18A). Chimera A had 7 substitutions (at positions 515, 539, 607, 644, 648, 654 and 687) in the sequence from the beginning of the gp41 to the transmembrane domain (TM) of clone 86d. Chimera B contained 3 substitutions (at position G515V, A539V, and D607A) in the sequence from the beginning of the gp41 to upstream of the HR2 region of 86d. Chimera A and B both retained the dual-tropic phenotype. In contrast, chimera C, with 5 substitutions (at position 746, 767, 787, 790, 812) in the cytoplasmic tail, and chimera D bearing the 5 substitutions in C plus 4 more changes (at position 644, 648, 654, 687) between HR2 and TM were R5-tropic (FIG. 18A).

Chimera B, with substitutions at positions 515, 539 and 607 relative to 10r, conferred a dual-tropic phenotype. However, the level of infection (RLU) of chimera B was much lower than the parental clone 86d or the chimera bearing the complete gp41 of 86d, indicating that accumulated substitutions in gp120 and the rest of gp41 may serve to reduce env mediated entry even though they did not confer the ability to use CXCR4 by themselves.

Figure 18B:
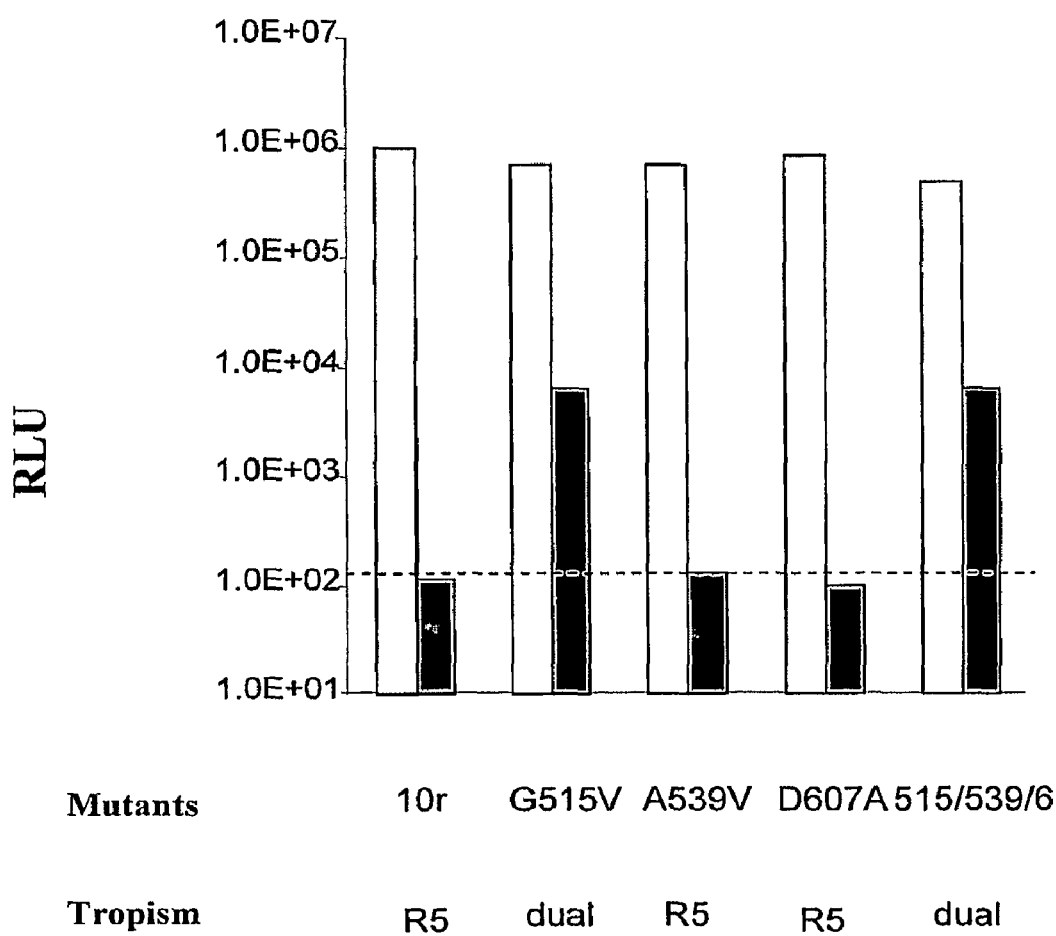

Each of the three substitutions (G515V, A539V or D607A) in Chimera B was introduced by site-directed mutagenesis into the env backbone of R5-tropic clone 10r (FIG. 18B). The G515V mutant env conferred dual-tropic phenotype. 515V was also presented in dual-X clones 11d and 88d. While the A539V or D607A clone 10r mutants remained exclusively R5-tropic in the context of the env backbone of R5-tropic clone 10r, 539V was presented in dual-X clones 11d, 88d and X4 clone 42x, and 607A was presented in dual-X clone 11d and X4 clone 42x. As such, 539V or 607A may affect the ability of HIV-1 to enter cells via the CXCR-4 co-receptor in the context, e.g., of an env backbone other than that of 10r.

Figure 18C:
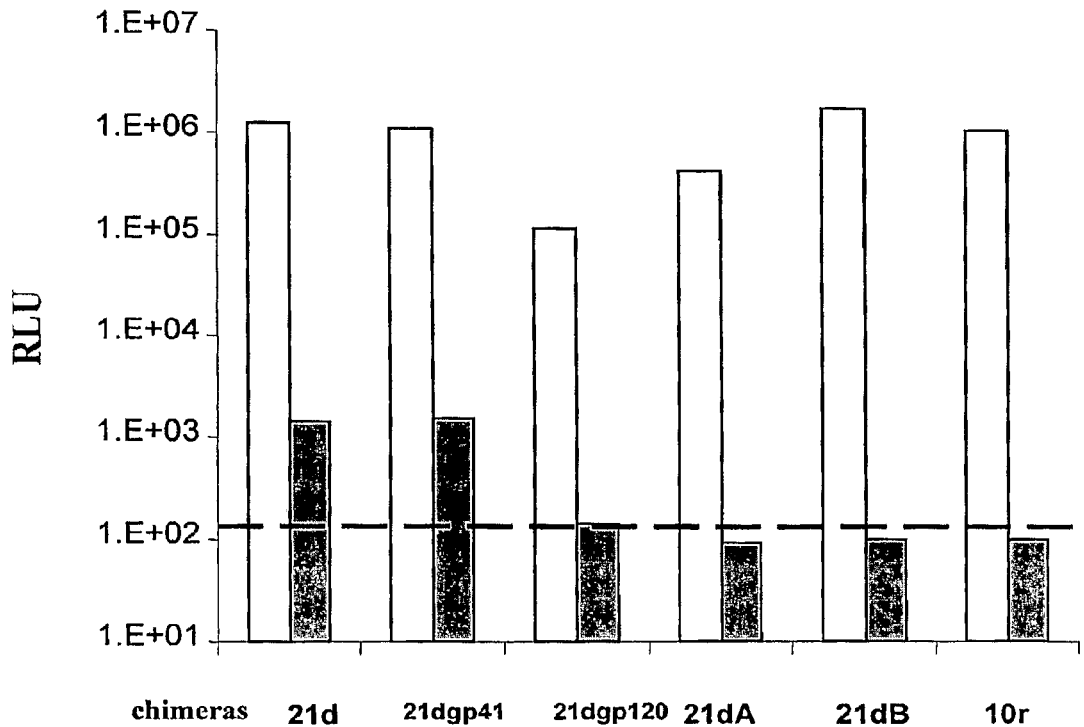

For dual-R clone 21d, no different substitution was found at position 515, but there were five substitutions in gp41 compared to clone 10r (at position 529, 539, 767, 787 and 792). Both chimera 21dA with 2 substitutions (T529A and A539V) in fusion peptide, or chimera 21 dB, with 3 substitutions (C767S, H787R and I792S) in cytoplasmic tail from clone 21, were unable to infect CXCR4 target cells but retained infectivity on CCR5 target cells (FIG. 18C). These results indicated that sequence changes in both fusion peptide and cytoplasmic tail of gp41, particularly at positions 529, 539, 767, 787, and/or 792, contributed to CXCR4 use by the dual-R clone 21d.

Whether dual-R clones with CXCR4 determinants in gp41 could alter fusogenic activity compared to env clones that use exclusively CCR5 was next assessed. The fusion results of dual-R, R5- X4- and dual-X tropic clones are summarized in Table 6. Compared to R5-tropic clone 10r, 7-fold higher fusion was observed with the dual-R clone 86d, but no enhanced fusion was observed for dual-R clone 21d, dual-X clone 88d, or X4-tropic clone 42x, with dual-X clone 11D, with substitution R3D in V3, exhibiting the highest fusion activity among these clones.

Sequence changes in env gp41 can alter the sensitivity to fusion inhibitor enfuvirtide (ENF) and mutations resistant to ENF are presented in HR1 domain in gp41. Whether dual-R clones with CXCR4 determinants in gp41 also affect sensitivity to ENF was determined (Table 6). Both dual-R clone 86d and 21d showed 4-5 fold-reduced susceptibility to ENF compared to both R5-, X4- and dual-X tropic clones without any amino acid changes in the HR1 domain. Both dual-R clone 21d and 86d showed similar sensitivity to X4 inhibitor AMD3100 (AnorMED, Inc.) compared to dual-X clones, whereas X4 clone 42d displayed subtle reduction in sensitivity to the X4 inhibitor. The dual-R clones also had similar sensitivity to R5 inhibitor L83 (Merck, Inc.) compared to R5 and X4-using clones, except that clone 88D appeared to be more sensitive to the R5 inhibitor which may associate with its lower infectivity on CCR5 target cells.

8. REFERENCES

Adachi, A., H. E. Gendelman, S. Koenig, T. Folks, R. Caney, A. Rabson, and M. A. Martin. 1986. Production of Acquired Immunodeficiency Syndrome-associated Retrovirus in Human and Nonhuman Cells Transfected with an Infectious Molecular Clone. *J. Virol.* 59:284-291.

Alkhatib, G., C. Combadiere, C. C. Broder, Y. Feng, P. E. Kennedy, P. M. Murphy, and E. A. Berger. 1996. CC CKR5: A Rantes, MIP-1alpha, MIP-1 Beta Receptor as a Fusion Cofactor for Macrophage-tropic HIV-1. *Science* 272:1955-8.

Allaway G. P., Ryder A. M., Beaudry G. A., and Maddon P. J. 1993. Synergistic Inhibition of HIV-1 Envelope-Mediated Cell Fusion by CD4-based Molecules in Combination with Antibodies to Gp120 or Gp41. *Aids Res. Hum. Retroviruses* 9:581-7.

Baba, M., O, Nishimura, N. Kanzaki, M. Okamoto, H. Sawada, Y. Iizawa, M. Shiraishi, Y. Aramaki, K. Okonogi, Y. Ogawa, K. Meguro, and M. Fujino. 1999. A Small-molecule, Nonpeptide CCR5 Antagonist with Highly Potent and Selective Anti-hiv-1 Activity. *Proc. Natl. Acad. Sci. USA* 96:5698-703.

Baxter, J., D. Mayers, D. Wentworth, J. Neaton, and T. Merigan. 1999. A Pilot Study of the Short-term Effects of Antiretroviral Management Based on Plasma Genotypic Antiretroviral Resistance Testing (Gart) in Subjects Failing Antiretroviral Therapy. *Presented at the 6th Conference on Retroviruses and Opportunistic Infections*. Chicago, Ill.

Bernard P., Kezdy K. e., Van Melderen L., Steyaert J., Wyns L., Pato M. L., Higgins P. N., and Couturier M. 1993. The F Plasmid CcdB protein Induces Efficient ATP-dependent Dna Cleavage by Gyrase. *J. Mol. Biol.* 23:534-41.

Bernard, P. and Couturier, M. 1992. Cell Killing by the F Plasmid Ccdb protein Involves Poisoning of DNAtopoisomerase II Complexes. *J. Mol. Bio.* 226:735-45.

Bleul, C. C., M. Farzan, H. Choe, C. Parolin, I. Clark-Lewis, J. Sodroski, and T. A. Springer. 1996. The Lymphocyte Chemoattractant Sdf-1 Is a Ligand for Lestr/fusin and Blocks Hiv-1 Entry. *Nature* 382:829-33.

Bridger G. J, Skerlj R. T., Padmanabhan S., Martellucci S. A., Henson G. W., Struyf S., Witvrouw M., Schols D., and De Clercq E. 1999. Synthesis and Structure-activity Relationships of Phenylenebis(methylene)-linked Bis-azamacrocycles That Inhibit HIV-1 and HIV-2 Replication by Antagonism of the Chemokine Receptor CXCR4. *J. Med. Chem.* 42:3971-81.

Brummer Z L, Dong W W, YipB. Wynhoven B, Hoffman N G, Swanstrom R. Jensen M A, Mullins J I, Hogg R S, Montaner J S. Harrigan P R. 2004. Clinical and Immunological Impace of HIV Envelop V3 Sequence Variation After Starting Initial Triple Antiretroviral Therapy. *AIDS* 18:F1-9.

Carpenter, C. J., Cooper D. A., Fischl, M. A., Gatell J. M., Gazzard B. G., Hammer S. M., Hirsch M. S., Jacobsen D. M., Katzenstein D. A., Montaner J. S., Richman D., Saag M. S., Schechter M., Schooley R. T., Thompson M. A., Vello S., Yeni P. G., and Volberding P. A. 2000. Antiretroviral Therapy in Adults. *JAMA* 283:381-89.

CDC (Centers for Disease Control and Prevention). HIV/AIDS Surveillance Report, 1999; 11 (no. 1).

Coffin, J. M. 1995. HIV Population Dynamics in Vivo: Implications for Genetic Variation, Pathogenesis, and Therapy. *Science* 267:483-489.

DHHS (Department of Health and Human Services). Henry Kaiser Family Foundation: Guidelines for the Use of Antiretrovirals Agents in HIV-infected Adults and Adolescents. (Jan. 28, 2000).

Gerdes, K., L. K. Poulsen. T. Thisted, A. K. Nielson, J. Martinussen, and P. H. Andreasen. 1990. The Hok Killer Gene Family in Gram-negative Bacteria. *The New Biologist:* 2:946-956.

Hertogs, K., M. P. De Bethune, V. Miller, T. Ivens, P. Schel, A. V. Cauwenberge, C. Van Den Eynde, V. Van Gerwen, H. Azijn, M. Van Houtte, F. Peeters, S. Staszewski, M. Conant, S. Bloor, S. Kemp, B. Larder, and R. Pauwels. 1998. A Rapid Method for Simultaneous Detection of Phenotypic Resistance to Inhibitors of protease and Reverse Transcriptase in Recombinant Human Immunodeficiency Virus Type 1 Isolates from Subjects Treated with Antiretroviral Drugs. *Antimicrob. Agents Chemother.* 42:269-276.

Hwang, J.-j., L. Li, W. f. Anderson. 1997. A Conditional Self-inactivating Retrovirus Vector That Uses a Tetracycline-responsive Expression System. *J. Virol.* 71: 7128-7131.

Japour, A. J., D. L. Mayers, V. A. Johnson, D. R. Kuritzkes, L. A. Beckett, J. M. Arduino, J. Lane, B. R. J., P. S. Reichelderfer, R. T. D-aquila, C. S. Crumpacker, T. R.-S. Group, T.A.C.T. Group, and V.C.R.W. Group. 1993. Standardized Peripheral Blood Mononuclear Cell Culture Assay for Determination of Drug Susceptibilities of Clinical Human Immunodefiency Virus Type 1 Isolates. Antimicrob. Agents Chemother. 37:1095-1101.

Jensen M A, Li F S, van't Wout A B, Nickle D C, Shriner D, He H X, McLaughlin S, Shankarappa R. Margolick J B, Mullins J I. 2003, J. Viorlogy 77:13376-13388

Judice J. K., Tom J. Y., Huang W., Wrin T., Vennari J., Petropoulos C. J., and Mcdowell R. S. 1997. Inhibition HIV Type 1 Infectivity by Constrained Alphahelical Peptides: Implications for the Viral Fusion Mechanism. *Proc. Natl. Acad. Sci. U S A* 94:13426-30.

Kilby J M, Hopkins S, Venetta T m, Dimassimo B, Cloud G a, Lee J y, Alldrdge L, Hunter E, Lambert D, Bolognesi D, Matthews T, Johnson M r. Nowak M a, Shaw G m, and Saag M s. 1998. Potent Suppression of HIV-1 Replication in Humans by T-20, a Peptide Inhibitor of Gp41-mediated Virus Entry. *Nat. Med.* 4:1302-7.

Kumar S, Tamura K, Nei M. 2004. Mega3: Integrated Software for Molecular Evolutionary Genetics Analysis and Sequence Alignment. Brief Bioinform 5(2):150-163

Mascola, J. R., G. Stiegler, T. C. Vancott, H. Katinger, C. B. Carpenter, C. E. Hanson, H. Beary, D. Hayes, S. S. Frankel, D. L. Birx, and M. G. Lewis. 2000. Protection of Macaques Against Vaginal Transmission of a Pathogenic HIV-1/siv Chimeric Virus by Passive Infusion of Neutralizing Antibodies. Nature Med. 6:207-210.

Miyoshi, H., B. Ulrike, M. Takahashi, F. H. Gage, and I. M. Verma. 1998. Development of a Self-inactivating Lentivirus Vector. J. Virol. 72:8150-5157.

Naviaux, R. K., E. Costanzi, M. Haas, and I. M. Verma. 1996. The Pcl Vector System: Rapid production of Helper-free, High-titer, Recombinant Retroviruses. J. Virol. 70: 5701-5705.

Petropoulos, C. J., N. T. Parkin, K. L. Limoli, Y. S. Lie, T. Wrin, W. Huang, H. Tian, D. Smith, G. A. Winslow, D. Capon and J. M. Whitcomb. 2000. A Novel Phenotypic Drug Susceptibility Assay for HIV-1. Antimicrob. Agents & Chem. 44:920-928.

Phrrma (Pharmaceutical Research and Manufacturers of America). New Medicines in Development for Aids 1999.

Piketty, C., E. Race, P. Castiel, L. Belec, G. Peytavin, A. si-mohamed, G. Gonzalez-canali, L. Weiss, F. Clavel, and M. Kazatchkine. 1999. Efficacy of a Five-drug Combination Including Ritonavir, Saquinavir and Efavirenz in Subjects Who Failed on a Conventional Triple-drug Regimen: Phenotypic Resistance to protease Inhibitors predicts Outcome of Therapy. Aids: 13:f71-f77.

Porter, C. C., K. V. Lukacs, G. Box, Y. Takeuchi, and M. K. L. Collins. 1998. Cationic Liposomes Enhance the Rate of Transduction by a Recombinant Retroviral Vector in Vitro and in Vivo. J. Virol. 72:4832-4840.

Reimann K. A., Cate R. L., Wu Y., Palmer L., Olson D., Waite B. C., Letvin N. L., and Burkly L. C. 1995. In Vivo Administration of CD4-specific Monoclonal Antibody: Effect on provirus Load in Rhesus Monkeys Chronically Infected with the Simian Immunodeficiency Virus of Macaques. *Aids Res. Hum. Retroviruses* 11:517-25.

Retroviruses. Coffin, J., S. Hughes, H. Varmus (Eds). 1997. Cold Spring Harbor Laboratory Press, Cold Spring Harbor, N.Y.

Richman, D. 1998. Nailing down Another HIV Target. Nature Med. 4:1232-1233.

Rimsky, L. T., D. C. Shugars, and T. J. Matthews. 1998. Determinants of Human Immunodeficiency Virus Type 1 Resistance to Gp41-derived Inhibitory Peptides. J. Virol. 72:986-993.

Rodriguez-Rosado, R., Briones, C. and Soriano, V. 1999. Introduction of HIV Drug-resistance Testing in Clinical Practice. Aids 13:1007-1014.

Sarkar G and Sommer S S, 1990, The "Megaprimer" Method of Site-Directed Mutagenesis. Biotechniques 8:404-40

Schinazi, R. F., Larder, B. A., and Mellors, J. W. 1999. Mutations in Retroviral Genes Associated with Drug Resistance. Intl. Antiviral News: 7:46-49.

Shi C., and J. W. Mellors. 1997. A Recombinant Retroviral System for Rapid in Vivo Analysis of Human Immunodefiency Virus Type 1 Susceptibility to Reverse Transcriptase Inhibitors. Antimicrob. Agents Chemother 41:2781-2785.

Schurmann D et al. SCH D: antiviral activity of a CCR5 receptor antagonist. Eleventh Conference on Retroviruses and Opportunistic Infections, San Francisco, abstract 140LB, 2004.

Stephenson, J. 1999. New Class of Anti-HIV Drugs. Jama 282:1994.

Who, Unaids/World Health Organization. Report: Aids Epidemic Update: December 1999.

Wild, C., T. Oak, C. Mcdanal, D. Bolognesi, and T. Matthews. 1992. A Synthetic Peptide Inhibitor of HIV Replication: Correlation Between Solution Structure and Viral Inhibition. *Proc. Natl. Acad. Sci. USA* 89:10537-10541.

Zennou, V., F. Mammamo, S. Paulous, D. Mathez, and F. Calvel. 1998. Loss of Viral Fitness Associated with Multiple Gag and Gag-pol processing Defects in Human Immunodefiency Virus Type 1 Variants Selected for Resistance to Protease Inhibitors in vivo. *J. Virol:* 72:3300-06.

Ziermann, R., K. Limoli, K. Das, E. Arnold, C. J. Petropoulos, and N. T. Parkin. 2000. A Mutation in HIV-1 Protease, N88s, That Causes in Vitro Hypersensitivity to Amprenavir. *J. Virol.* 74:4414-4419.

TABLE 1

| Cells | |
|---|---|
| Cell | Receptor |
| 5.25 | CXCR4, CD4, CCR5 (not expressed well) BONZO |
| 5.25.Luc4.M7 | CD4, CCR5, BONZO |
| HOS.CD4.CCR5 | CD4, CCR5 |
| HOS.CD4.CXCR4 | CD4, CXCR4 |
| HOS.CD4 | CD4, low level expression of CCR5 and CXCR4 |
| HOS HT4 R5 GFP wt | CD4, CXCR4, CCR5 |
| HOS.CD4.CCR5.GFP.M7#6* | CD4, CXCR4, CCR5 |
| P4.CCR5 | CD4, CXCR4, CCR5 |
| U87.CD4 | CD4 |
| U87.CD4 R5 | CD4, CCR5 |

TABLE 1-continued

Cells

| Cell | Receptor |
|---|---|
| U87.CD4 X4 | CD4, CXCR4 |
| MT2 | CD4, CXCR4 |
| MT4 | CD4, CXCR4 |
| PM1 | CD4, CXCR4, CCR5 |
| CEM NKr CCR5 | CD4, CXCR4, CCR5 |

TABLE 2

Representative viruses and reagents

| Viruses | Envelope[a] | Source |
|---|---|---|
| 89.6, SF2 | R5-X4/SI/B | ARRRP[b] |
| 92BR014, 92US076 | R5-X4/SI/B | ARRRP |
| JR-CSF, 91US005 | R5/NSI/B | ARRRP |
| 91US054 | SI/B | ARRRP |
| NL43, MN, ELI | X4/B | ARRRP |
| 92HT599 | X4 | ARRRP |
| 92UG031 | R5/NSI/A | ARRRP |
| 92TH014, 92TH026 | R5/NSI/B | ARRRP |
| 92BR025, 93MW959 | R5/SI/C | ARRRP |
| 92UG035 | R5/NSI/D | ARRRP |
| 92TH022, 92TH023 | R5/NSI/E | ARRRP |
| 93BR020 | R5-X4/SI/F | ARRRP |
| Antibodies | Epitope | SOURCE |
| Mabs 2F5, 1577 | gp4I TM | ARRRP |
| Mabs IG1b12, 2G12, 17b, 48D | gp120 SU | ARRRP |
| Neutralization sera #2, HIV-IG | Polyclonal | ARRRP |
| Entry inhibitors | Target | Source |
| CD4-IG | gp120 SU | Genentech |
| CD4-IGG2 | gp120 SU | Adarc |
| SCD4 (PRO 542) | Sigma | Progenics |
| T20 (DP178) | gp41 TM | Trimeris |
| Rantes, MIPla/b | CCR5 | SIGMA/ARRRP |
| SDFla/b | CXCR4 | SIGMA/ARRRP |
| AMD 3100 | CXCR4 | AnorMed |
| Dextran sulfate, Heparin | Non-specific | Sigma |

[a] R5 (CCR5 co-receptor), X4 (CXCR4 co-receptor) SI (syncytium inducing), NSI (non-syncytium inducing), A, B, C, D, E, F (envelope clade designation)
[b] AIDS Research and Reference Reagent Program

TABLE 3

| | Primers Tested for the Amplification of HIV Envelope | SEQ ID NO: |
|---|---|---|
| | RT PRIMERS | |
| Primer 1 | 5'-GGA GCA TTT ACA AGC AGC AAC ACA GC-3' | 1 |
| Primer 2 | 5'-TTC CAG TCA VAC CTC AGG TAC-3' | 2 |
| Primer 3 | 5'-AGA CCA ATG ACT TAY AAG G-3' | 3 |
| | 5' PCR PRIMERS | |
| Primer 4 | 5'-GGG CTC GAG ACC GGT CAG TGG CAA TGA GAG TGA AG-3' | 4 |
| Primer 5 | 5'-GGG CTC GAG ACC GGT GAG CAG AAG ACA GTG GCA ATG A-3' | 5 |
| Primer 6 | 5'-GGG CTC GAG ACC GGT GAG CAG AAG ACA GTG GCA ATG-3' | 6 |
| | 3' PCR PRIMERS | |
| Primer 7 | 5'-GGG TCT AGA ACG CGT TGC CAC CCA TCT TAT AGC AA-3' | 7 |
| Primer 8 | 5'-GGG TCT AGA ACG CGT CCA CTT GCC ACC CAT BTT ATA GC-3' | 8 |
| Primer 9 | 5'-GGG TCT AGA ACG CGT CCA CTT GCC ACC CAT BTT A-3' | 9 |
| Primer 10 | 5'-GAT GGT CTA GAA CGC TGT TCA ATA TCC TGC CTA ACT C-3' | 10 |

TABLE 4

Analysis of twenty two env clones from a single patient sample

| Env clone | Tropism | R5 RLU | X4 RLU | V3 amino acid sequences (SEQ ID NO:) | 11/25 rule | PSSM |
|---|---|---|---|---|---|---|
| b3 55r | R5 | 158594 | 60 | CTRPGNNTRRSITMGPGRAFYTTGEIIGDIRKAHC (11) | R5 | R5 |
| b3 c2r | R5 | 1082926 | 69 | | R5 | R5 |
| 8r | R5 | 273662 | 67 | ................................... (11) | R5 | R5 |
| 5r | R5 | 145655 | 74 | ................................... (11) | R5 | R5 |
| 25r | R5 | 735520 | 144 | ................................... (11) | R5 | R5 |
| 15r | R5 | 293016 | 145 | ................................... (11) | R5 | R5 |
| b3 79r | R5 | 1898438 | 101 | ................................... (11) | R5 | R5 |
| 10r* | R5 | 1149479 | 102 | ................................... (11) | R5 | R5 |
| 13d | dual-R | 214029 | 798 | ................................... (11) | R5 | R5 |
| 23d | dual-R | 705068 | 805 | ................................... (11) | R5 | R5 |
| 22d | dual-R | 1985072 | 841 | ................................... (11) | R5 | R5 |
| 21d* | dual-R | 1278284 | 1426 | ................................... (11) | R5 | R5 |
| b2 86d* | dual-R | 3790005 | 63759 | ................................... (11) | R5 | R5 |
| b3 88D | dual_X | 3145 | 130982 | ............H..-H.R....KN.......... (12) | R5 | R5 |
| b3 16D | dual_X | 19281 | 176477 | ............H..-H.R....KN.......... (12) | R5 | R5 |
| b3 73D | dual_X | 27100 | 329832 | ............H..-H.R....KN.......... (12) | R5 | R5 |
| b2 11D | dual_X | 16830 | 349224 | ............H..-H.R....KN.......... (12) | R5 | R5 |
| b3 67D | dual_X | 8862 | 413493 | ............H..-H.R....KN.......... (12) | R5 | R5 |
| 88D | dual_X | 8456 | 931105 | ............H..-H.R....KN.......... (12) | R5 | R5 |
| 56D | dual_X | 7114 | 963659 | ............H..-H.R....KN.......... (12) | R5 | R5 |
| 11D* | dual_X | 11893 | 27700 | ..G.........H..-H.R....KN.......... (13) | R5 | R5 |
| 42x* | X4 | 71 | 328864 | ......S...G.LV.-T.R....RN.......... (14) | R5 | R5 |

TABLE 5

Comparison of amino acid sequences in env sequences outside of the V3 Loop

Amino acid identity at in indicated position (according to HXB2)

| AA position | 3 | 4 | 16 | 37 | 84 | 92 | 121 | 141 | 146 | 148 | 152 | 175 | 184 |
|---|---|---|---|---|---|---|---|---|---|---|---|---|---|
| env region | C1 | C1 | C1 | C1 | C1 | C1 | C1 | V1 | V1 | V1 | V1 | V2 | V2 |
| 10r | G | M | N | A | L | N | K | N | – | G | E | F | V |
| 21d | V | M | N | T | L | N | K | N | – | G | E | F | I |
| b2_86d | V | M | K | T | L | N | K | N | – | G | G | F | I |
| 11D | V | M | K | T | L | N | K | N | – | G | E | L | I |
| 88D | V | M | K | T | L | N | E | N | – | G | E | L | I |
| b1_c42x | V | T | K | T | I | S | K | S | R | E | E | I | I |

| AA position | 279 | 281 | 287 | 290 | 295 | 337 | 348 | 361 | 389 | 403 | 405 | 406 | 485 |
|---|---|---|---|---|---|---|---|---|---|---|---|---|---|
| env region | C2 | C2 | C2 | C2 | C2 | C3 | C3 | C3 | V4 | V4 | V4 | V4 | C5 |
| 10r | N | A | Q | E | N | T | K | T | I | E | P | N | K |
| 21d | N | A | R | E | N | T | E | I | I | E | P | N | K |
| b2_86d | N | A | Q | E | N | V | E | I | R | E | S | K | E |
| 11D | N | A | Q | E | N | V | E | I | R | E | S | N | E |
| 88D | N | A | Q | E | N | V | E | I | R | E | S | N | E |
| b1_c42x | D | T | Q | K | K | V | E | I | I | G | S | N | K |

Amino acid identity at in indicated position (according to HXB2)

| AA position | 515 | 529 | 539 | 607 | 644 | 648 | 654 | 687 | 746 | 767 | 787 | 790 | 792 | 812 | 815 | 817 | 818 |
|---|---|---|---|---|---|---|---|---|---|---|---|---|---|---|---|---|---|
| env region | FP | FP | FP | HR1-HR2 | HR2 | HR2 | HR2 | TM | CT | CT | CT | CT | CT | CT | CT | CT | CT |
| 10r | G | T | A | D | T | D | E | M | G | C | H | W | I | I | F | A | I |
| 21d | G | A | V | D | T | D | E | M | G | S | R | W | S | I | F | A | I |
| b2_86d | V | A | V | A | N | E | D | I | E | S | R | R | I | V | F | A | I |
| 11D | V | A | V | A | N | E | D | I | E | S | H | W | I | I | F | A | I |
| 88D | V | A | V | D | T | D | E | M | G | S | R | W | S | I | F | A | I |
| b1_c42x | G | A | V | A | T | D | E | M | E | S | R | W | I | V | L | V | T |

 Substitution are presented in R5 clone 10r, not in other R5 clones

 Substitution are presented in X4-using clones, not R5 clones

| clones | Tropism | V3 | gp120 | gp41 | gp160 |
|---|---|---|---|---|---|
| 10r | R5 | | | | |
| 21d | dual-R | | 6 | 5 | 11 |
| b2_86d | dual-R | | 12 | 12 | 24 |
| 11D | dual-X | 7 | 11 | 10 | 28 |
| 88D | dual-X | 6 | 12 | 6 | 24 |
| b1_c42x | X4 | 9 | 20 | 10 | 39 |

TABLE 6

Sensitivity of Entry Inhibitors

| Clone | Tropism | L83 | AMD | T20 | Fusion |
|---|---|---|---|---|---|
| c10 | R5 | 0.0044 | | 0.0467 | 846 |
| c21 | dual-R | 0.0038 | nd | 0.2724 | 251 |
| c86 | dual-R | 0.0036 | 0.0056 | 0.2048 | 6163 |
| c88 | dual | 0.0012 | 0.0087 | 0.0277 | 443 |

TABLE 6-continued

Sensitivity of Entry Inhibitors

| Clone | Tropism | L83 | AMD | T20 | Fusion |
|---|---|---|---|---|---|
| c11 | dual | 0.0044 | 0.0034 | 0.0217 | 22115 |
| c42 | X4 | | 0.0458 | 0.0191 | 184 |

What is claimed is:

1. A method for determining whether an HIV is likely to have enhanced ability to enter a cell expressing CD4 and CXCR4 relative to a reference HIV, comprising detecting in a nucleic acid encoding an envelope protein of the HIV, a mutation encoding a valine substitution for glycine corresponding to position 515 of HIV strain HXB2, wherein the presence of the mutation indicates that the HIV is likely to have enhanced ability to enter a cell expressing CD4 and CXCR4 relative to a reference HIV.

2. The method of claim 1, wherein the reference HIV is NL4-3, HXB2, or SF2.

3. The method of claim 1, wherein the reference HIV has an envelope gene that encodes an envelope protein having a sequence identical to the envelope protein of the HIV except for a difference at a codon corresponding to codon 515 of HIV strain HXB2.

4. A method for determining whether an HIV is likely to have reduced ability to enter a cell expressing CD4 and CCR5 relative to a reference HIV, comprising detecting, in a nucleic acid encoding an envelope protein of the HIV, a mutation encoding a valine substitution for glycine corresponding to position 515 of HIV strain HXB2, wherein the presence of the mutation indicates that the HIV is likely to have reduced ability to enter a cell expressing CD4 and CCR5 relative to a reference HIV.

5. The method of claim 4, wherein the reference HIV is NL4-3, HXB2, or SF2.

6. The method of claim 1, wherein the reference HIV has an envelope gene that encodes an envelope protein having a sequence identical to the envelope protein of the HIV except for a difference at a codon corresponding to codon 515 of HIV strain HXB2.

* * * * *

UNITED STATES PATENT AND TRADEMARK OFFICE
CERTIFICATE OF CORRECTION

PATENT NO. : 8,114,585 B2
APPLICATION NO. : 12/304418
DATED : February 14, 2012
INVENTOR(S) : Wei Huang It is certified that error appears in the above-identified patent and that said Letters Patent is hereby corrected as shown below:

Title Page 2, item (56); Column 2, Line 44, Please delete "Iin", please insert -- In --.

Column 3, Line 33, Please delete "ACT", please insert -- ΔCT --.

Column 4, Line 9, Please delete "α-axis log 10 scale).", please insert -- (x-axis log 10 scale). --.

Column 7, Line 16, Please delete "lie", please insert -- Ile --.

Column 10, Line 33, Please delete "488-403", please insert -- 488403 --.

Column 10, Line 49, Please delete "488-403", please insert -- 488403 --.

Column 16, Line 28, Please delete "P is", please insert -- Pls --.

Column 18, Line 27, Please delete "(gp41™)", please insert -- (gp41TM) --.

Column 19, Line 12, Please delete "2.5", please insert -- ~2.5 --.

Column 19, Line 20, Please delete "MluT", please insert-- MluI --.

Column 27, Line 11, Please delete "Brumnuer", please insert -- Brummer --.

Column 31, Line 24, Please delete "Viorlogy", please insert -- Virology --.

Signed and Sealed this
Twenty-fourth Day of July, 2012

David J. Kappos
*Director of the United States Patent and Trademark Office*